(12) United States Patent
Le et al.

(10) Patent No.: US 10,441,419 B2
(45) Date of Patent: Oct. 15, 2019

(54) LOW PROFILE DELIVERY SYSTEM FOR TRANSCATHETER HEART VALVE

(71) Applicant: Edwards Lifesciences Corporation, Irvine, CA (US)

(72) Inventors: Thanh Huy Le, Oceanside, CA (US); Tri D. Tran, Fountain Valley, CA (US); Ronaldo C. Cayabyab, Mission Viejo, CA (US); David M. Taylor, Lake Forest, CA (US); Antonio O. Vidal, Tustin, CA (US); Robert Bowes, Trabuco Canyon, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 16/197,245

(22) Filed: Nov. 20, 2018

(65) Prior Publication Data
US 2019/0083260 A1    Mar. 21, 2019

Related U.S. Application Data

(63) Continuation of application No. 14/736,117, filed on Jun. 10, 2015, which is a continuation of application
(Continued)

(51) Int. Cl.
*A61F 2/24* (2006.01)
*A61M 25/10* (2013.01)
(Continued)

(52) U.S. Cl.
CPC .......... *A61F 2/2433* (2013.01); *A61M 25/01* (2013.01); *A61M 25/0147* (2013.01);
(Continued)

(58) Field of Classification Search
CPC .......... A61F 2/24; A61F 2/958; A61F 2/2427; A61F 2/2433; A61M 25/10;
(Continued)

(56) References Cited

U.S. PATENT DOCUMENTS

| 3,657,744 A | 4/1972 | Ersek |
| 4,035,849 A | 7/1977 | Angell et al. |

(Continued)

FOREIGN PATENT DOCUMENTS

| DE | 19532846 A1 | 3/1997 |
| DE | 19907646 A1 | 8/2000 |

(Continued)

*Primary Examiner* — Dianne Dornbusch
(74) *Attorney, Agent, or Firm* — Klarquist Sparkman, LLC; Joel B. German

(57) ABSTRACT

A method of delivery a prosthetic heart valve includes inserting a delivery apparatus and a prosthetic heart valve into a patient's vasculature. The delivery apparatus includes a steerable guide catheter, a balloon catheter, and a flex indicator. The balloon catheter extends coaxially through the guide catheter, the prosthetic heart valve is mounted on a distal end portion of the balloon catheter, and the flex indicator is movably coupled to a handle of the guide catheter. The method further includes adjusting flexion of a steerable section of the guide catheter to position the prosthetic heart valve. The flex indicator moves relative to the handle of the guide catheter as the flexion of the steerable section is adjusted, and the handle comprises one or more visual indicators adjacent the flex indicator to provide visual indication of an amount of flexion of the steerable section of the guide catheter.

16 Claims, 22 Drawing Sheets

Related U.S. Application Data

No. 12/247,846, filed on Oct. 8, 2008, now Pat. No. 9,061,119.

(60) Provisional application No. 61/083,117, filed on Jul. 23, 2008, provisional application No. 61/052,009, filed on May 9, 2008.

(51) Int. Cl.
*A61M 25/01* (2006.01)
*A61F 2/95* (2013.01)
*A61M 25/06* (2006.01)

(52) U.S. Cl.
CPC ........... *A61M 25/10* (2013.01); *A61F 2/2418* (2013.01); *A61F 2/2427* (2013.01); *A61F 2002/9517* (2013.01); *A61M 25/0105* (2013.01); *A61M 2025/0681* (2013.01); *A61M 2025/1093* (2013.01)

(58) Field of Classification Search
CPC .......... A61M 25/0136; A61M 25/0147; A61B 2017/003; A61B 2017/00318; A61B 2017/00323; A61B 2017/00327
See application file for complete search history.

(56) References Cited

U.S. PATENT DOCUMENTS

| | | | |
|---|---|---|---|
| 4,586,923 A | 5/1986 | Gould et al. | |
| 4,592,340 A | 6/1986 | Boyles | |
| 4,955,895 A | 9/1990 | Sugiyama et al. | |
| 4,994,077 A | 2/1991 | Dobben | |
| 5,002,560 A * | 3/1991 | Machold | A61F 2/90 604/104 |
| 5,030,204 A | 7/1991 | Badger et al. | |
| 5,059,177 A | 10/1991 | Towne et al. | |
| 5,176,698 A | 1/1993 | Burns et al. | |
| 5,192,297 A | 3/1993 | Hull | |
| 5,228,441 A * | 7/1993 | Lundquist | A61B 18/1492 600/380 |
| 5,266,073 A | 11/1993 | Wall | |
| 5,273,535 A * | 12/1993 | Edwards | A61M 25/0136 600/585 |
| 5,315,996 A * | 5/1994 | Lundquist | A61B 18/1492 600/374 |
| 5,322,064 A * | 6/1994 | Lundquist | A61B 18/1492 600/381 |
| 5,325,845 A | 7/1994 | Adair | |
| 5,328,467 A * | 7/1994 | Edwards | A61M 25/0138 600/373 |
| 5,342,299 A * | 8/1994 | Snoke | A61M 25/0136 600/146 |
| 5,346,498 A | 9/1994 | Greelis et al. | |
| 5,358,496 A | 10/1994 | Ortiz et al. | |
| 5,376,077 A * | 12/1994 | Gomringer | A61B 17/320758 604/167.06 |
| 5,411,552 A | 5/1995 | Andersen et al. | |
| 5,413,107 A * | 5/1995 | Oakley | A61B 8/12 600/463 |
| 5,441,483 A * | 8/1995 | Avitall | A61B 18/1492 604/95.05 |
| 5,458,615 A | 10/1995 | Klemm et al. | |
| 5,462,527 A * | 10/1995 | Stevens-Wright | A61B 18/1492 600/585 |
| 5,527,279 A * | 6/1996 | Imran | A61M 25/0158 604/95.01 |
| 5,545,209 A | 8/1996 | Roberts et al. | |
| 5,554,185 A | 9/1996 | Block et al. | |
| 5,591,195 A | 1/1997 | Taheri et al. | |
| 5,599,305 A | 2/1997 | Hermann et al. | |
| 5,601,568 A | 2/1997 | Chevillon et al. | |
| 5,632,760 A | 5/1997 | Sheiban et al. | |
| 5,639,274 A | 6/1997 | Fischell et al. | |
| 5,656,030 A * | 8/1997 | Hunjan | A61M 25/0136 604/264 |
| 5,707,376 A * | 1/1998 | Kavteladze | A61F 2/90 623/1.11 |
| 5,728,068 A | 3/1998 | Leone et al. | |
| 5,749,890 A | 5/1998 | Shaknovich | |
| 5,776,142 A | 7/1998 | Gunderson | |
| 5,782,809 A | 7/1998 | Umeno et al. | |
| 5,782,855 A | 7/1998 | Lau et al. | |
| 5,824,044 A | 10/1998 | Quiachon et al. | |
| 5,840,081 A | 11/1998 | Andersen et al. | |
| 5,891,154 A * | 4/1999 | Loeffler | A61F 2/958 606/194 |
| 5,904,667 A * | 5/1999 | Falwell | A61M 25/0147 600/146 |
| 5,906,619 A | 5/1999 | Olson et al. | |
| 5,908,405 A | 6/1999 | Imran et al. | |
| 5,916,147 A | 6/1999 | Boury | |
| 5,954,654 A * | 9/1999 | Eaton | A61B 1/0052 600/459 |
| 5,961,536 A | 10/1999 | Mickley et al. | |
| 5,968,068 A | 10/1999 | Dehdashtian et al. | |
| 5,984,907 A * | 11/1999 | McGee | A61M 25/0054 604/264 |
| 6,019,777 A | 2/2000 | Mackenzie | |
| 6,027,510 A | 2/2000 | Alt | |
| 6,033,378 A * | 3/2000 | Lundquist | A61M 25/0136 604/528 |
| 6,033,381 A | 3/2000 | Kontos | |
| 6,136,007 A | 10/2000 | Goldsteen et al. | |
| 6,143,016 A | 11/2000 | Bleam et al. | |
| 6,162,208 A | 12/2000 | Hipps | |
| 6,168,614 B1 | 1/2001 | Andersen et al. | |
| 6,174,327 B1 | 1/2001 | Mertens et al. | |
| 6,203,550 B1 | 3/2001 | Olson | |
| 6,217,585 B1 | 4/2001 | Houser et al. | |
| 6,235,050 B1 | 5/2001 | Quiachon et al. | |
| 6,251,092 B1 | 6/2001 | Qin et al. | |
| 6,251,093 B1 * | 6/2001 | Valley | A61B 17/12022 604/97.03 |
| 6,319,227 B1 * | 11/2001 | Mansouri-Ruiz | A61B 8/12 600/466 |
| 6,379,372 B1 | 4/2002 | Dehdashtian et al. | |
| 6,383,171 B1 | 5/2002 | Gifford et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,464,645 B1 * | 10/2002 | Park | A61B 1/0052 600/462 |
| 6,471,672 B1 | 10/2002 | Brown | |
| 6,500,147 B2 | 12/2002 | Omaleki et al. | |
| 6,514,228 B1 | 2/2003 | Hamilton et al. | |
| 6,527,979 B2 | 3/2003 | Constantz et al. | |
| 6,579,305 B1 | 6/2003 | Lashinski | |
| 6,582,462 B1 | 6/2003 | Andersen et al. | |
| 6,599,296 B1 | 7/2003 | Gillick et al. | |
| 6,652,578 B2 | 11/2003 | Bailey et al. | |
| 6,663,588 B2 * | 12/2003 | DuBois | A61M 25/0136 604/95.01 |
| 6,730,118 B2 | 5/2004 | Spenser et al. | |
| 6,733,525 B2 | 5/2004 | Yang et al. | |
| 6,764,504 B2 | 7/2004 | Wang et al. | |
| 6,767,362 B2 | 7/2004 | Schreck | |
| 6,776,765 B2 * | 8/2004 | Soukup | A61B 5/0086 600/435 |
| 6,830,584 B1 | 12/2004 | Seguin | |
| 6,893,460 B2 | 5/2005 | Spenser et al. | |
| 6,908,481 B2 | 6/2005 | Cribier | |
| 7,011,094 B2 | 3/2006 | Rapacki et al. | |
| 7,018,406 B2 | 3/2006 | Seguin et al. | |
| 7,018,408 B2 | 3/2006 | Bailey et al. | |
| 7,137,993 B2 | 11/2006 | Acosta et al. | |
| 7,276,084 B2 | 10/2007 | Yang et al. | |
| 7,294,135 B2 * | 11/2007 | Stephens | A61F 2/013 606/108 |
| 7,318,278 B2 | 1/2008 | Zhang et al. | |
| 7,320,702 B2 | 1/2008 | Hammersmark et al. | |

(56) References Cited

U.S. PATENT DOCUMENTS

| | | | |
|---|---|---|---|
| 7,320,704 B2 | 1/2008 | Lashinski et al. | |
| 7,374,571 B2 | 5/2008 | Pease | |
| 7,393,360 B2 | 7/2008 | Spenser et al. | |
| 7,435,257 B2 | 10/2008 | Lashinski et al. | |
| 7,506,650 B2 | 3/2009 | Lowe et al. | |
| 7,510,575 B2 | 3/2009 | Spenser et al. | |
| 7,550,001 B2 * | 6/2009 | Dorn | A61F 2/95 623/1.12 |
| 7,585,321 B2 | 9/2009 | Cribier | |
| 7,594,926 B2 | 9/2009 | Linder et al. | |
| 7,597,709 B2 | 10/2009 | Goodin | |
| 7,618,446 B2 | 11/2009 | Andersen et al. | |
| 7,780,723 B2 | 8/2010 | Taylor | |
| 7,785,366 B2 | 8/2010 | Maurer et al. | |
| 7,959,661 B2 | 6/2011 | Hijlkema et al. | |
| 8,029,556 B2 | 10/2011 | Rowe | |
| 8,167,932 B2 | 5/2012 | Bourang et al. | |
| RE43,882 E | 12/2012 | Hopkins et al. | |
| 8,449,606 B2 | 5/2013 | Eliasen et al. | |
| 8,475,523 B2 | 7/2013 | Duffy | |
| 8,568,472 B2 | 10/2013 | Marchand et al. | |
| 8,888,834 B2 * | 11/2014 | Hansen | A61F 2/95 623/1.11 |
| 9,061,119 B2 | 6/2015 | Le et al. | |
| 9,119,716 B2 | 9/2015 | Lee et al. | |
| 9,795,477 B2 | 10/2017 | Tran et al. | |
| 10,188,413 B1 * | 1/2019 | Morriss | A61B 17/24 |
| 2001/0002445 A1 | 5/2001 | Vesely | |
| 2001/0007082 A1 | 7/2001 | Dusbabek et al. | |
| 2001/0025134 A1 * | 9/2001 | Bon | A61M 25/0136 600/146 |
| 2002/0019591 A1 * | 2/2002 | Bon | A61M 25/0136 600/462 |
| 2002/0032481 A1 | 3/2002 | Gabbay | |
| 2002/0058995 A1 | 5/2002 | Stevens | |
| 2002/0111666 A1 | 8/2002 | Hart et al. | |
| 2002/0143302 A1 * | 10/2002 | Hinchliffe | A61B 18/00 604/272 |
| 2002/0165461 A1 | 11/2002 | Hayzelden et al. | |
| 2003/0004505 A1 * | 1/2003 | Bencini | A61B 18/1492 606/41 |
| 2003/0028236 A1 | 2/2003 | Gillick et al. | |
| 2003/0040792 A1 | 2/2003 | Gabbay | |
| 2003/0050694 A1 | 3/2003 | Yang et al. | |
| 2003/0074045 A1 * | 4/2003 | Buzzard | A61F 2/95 623/1.11 |
| 2003/0120341 A1 | 6/2003 | Shennib et al. | |
| 2003/0149467 A1 * | 8/2003 | Linder | A61F 2/013 623/1.11 |
| 2003/0167060 A1 | 9/2003 | Buzzard et al. | |
| 2003/0191516 A1 | 10/2003 | Weldon et al. | |
| 2004/0064179 A1 * | 4/2004 | Linder | A61F 2/013 623/1.11 |
| 2004/0093061 A1 | 5/2004 | Acosta et al. | |
| 2004/0133263 A1 | 7/2004 | Dusbabek et al. | |
| 2004/0143197 A1 | 7/2004 | Soukup et al. | |
| 2004/0153137 A1 | 8/2004 | Gaschino et al. | |
| 2004/0186563 A1 | 9/2004 | Lobbi | |
| 2004/0186565 A1 | 9/2004 | Schreck | |
| 2004/0230287 A1 | 11/2004 | Hartley et al. | |
| 2004/0260389 A1 | 12/2004 | Case et al. | |
| 2005/0027305 A1 | 2/2005 | Shiu et al. | |
| 2005/0027345 A1 | 2/2005 | Horan et al. | |
| 2005/0060016 A1 | 3/2005 | Wu et al. | |
| 2005/0080474 A1 | 4/2005 | Bernard et al. | |
| 2005/0080475 A1 | 4/2005 | Andreas et al. | |
| 2005/0080476 A1 * | 4/2005 | Gunderson | A61F 2/95 623/1.11 |
| 2005/0090890 A1 | 4/2005 | Wu et al. | |
| 2005/0096736 A1 | 5/2005 | Osse et al. | |
| 2005/0137689 A1 | 6/2005 | Salahieh et al. | |
| 2005/0149159 A1 | 7/2005 | Andreas et al. | |
| 2005/0149160 A1 | 7/2005 | McFerran | |
| 2005/0159728 A1 * | 7/2005 | Armour | A61M 25/0662 604/528 |
| 2005/0203614 A1 | 9/2005 | Forster et al. | |
| 2005/0203617 A1 | 9/2005 | Forster et al. | |
| 2005/0222603 A1 | 10/2005 | Andreas et al. | |
| 2005/0245894 A1 | 11/2005 | Zadno-Azizi | |
| 2005/0273151 A1 | 12/2005 | Fulkerson et al. | |
| 2005/0277875 A1 * | 12/2005 | Selkee | A61M 25/0136 604/95.04 |
| 2006/0025857 A1 | 2/2006 | Bergheim et al. | |
| 2006/0135961 A1 | 6/2006 | Rosenman et al. | |
| 2006/0276873 A1 | 12/2006 | Sato | |
| 2006/0282150 A1 | 12/2006 | Olson et al. | |
| 2007/0005131 A1 * | 1/2007 | Taylor | A61F 2/2433 623/2.11 |
| 2007/0016164 A1 * | 1/2007 | Dudney | A61M 25/0136 604/523 |
| 2007/0021767 A1 * | 1/2007 | Breznock | A61B 17/00234 606/185 |
| 2007/0073389 A1 | 3/2007 | Bolduc et al. | |
| 2007/0088431 A1 | 4/2007 | Bourang et al. | |
| 2007/0112422 A1 | 5/2007 | Dehdashtian | |
| 2007/0118201 A1 | 5/2007 | Pappas et al. | |
| 2007/0156224 A1 | 7/2007 | Cioanta et al. | |
| 2007/0156225 A1 | 7/2007 | George et al. | |
| 2007/0168014 A1 * | 7/2007 | Jimenez | A61F 2/95 623/1.12 |
| 2007/0191865 A1 * | 8/2007 | Pappas | A61F 2/966 606/108 |
| 2007/0203575 A1 | 8/2007 | Forster et al. | |
| 2007/0219612 A1 | 9/2007 | Andreas et al. | |
| 2007/0239251 A1 | 10/2007 | Chia et al. | |
| 2007/0244546 A1 | 10/2007 | Francis | |
| 2007/0260301 A1 | 11/2007 | Chuter et al. | |
| 2007/0265700 A1 | 11/2007 | Eliasen et al. | |
| 2008/0065011 A1 | 3/2008 | Marchand et al. | |
| 2008/0125853 A1 | 5/2008 | Bailey et al. | |
| 2008/0154190 A1 * | 6/2008 | St. Germain | A61M 25/0136 604/95.04 |
| 2008/0188920 A1 | 8/2008 | Moberg et al. | |
| 2008/0294230 A1 | 11/2008 | Parker | |
| 2009/0069889 A1 | 3/2009 | Suri et al. | |
| 2009/0138079 A1 | 5/2009 | Tuval et al. | |
| 2009/0157175 A1 | 6/2009 | Benichou | |
| 2009/0192585 A1 | 7/2009 | Bloom et al. | |
| 2009/0228093 A1 | 9/2009 | Taylor et al. | |
| 2009/0234428 A1 | 9/2009 | Snow et al. | |
| 2009/0276040 A1 | 11/2009 | Rowe et al. | |
| 2009/0281619 A1 * | 11/2009 | Le | A61M 25/01 623/2.11 |
| 2009/0299456 A1 | 12/2009 | Melsheimer | |
| 2009/0319037 A1 | 12/2009 | Rowe et al. | |
| 2010/0004633 A1 * | 1/2010 | Rothe | A61M 25/0082 604/528 |
| 2010/0030318 A1 | 2/2010 | Berra | |
| 2010/0036472 A1 | 2/2010 | Papp | |
| 2010/0036473 A1 | 2/2010 | Roth | |
| 2010/0049313 A1 | 2/2010 | Alon et al. | |
| 2010/0076402 A1 | 3/2010 | Mazzone et al. | |
| 2010/0076541 A1 | 3/2010 | Kumoyama | |
| 2010/0082089 A1 | 4/2010 | Quadri et al. | |
| 2010/0087811 A1 * | 4/2010 | Herrin | A61B 17/0057 606/40 |
| 2010/0094394 A1 | 4/2010 | Beach et al. | |
| 2010/0121425 A1 | 5/2010 | Shimada | |
| 2010/0145431 A1 | 6/2010 | Wu et al. | |
| 2010/0161036 A1 * | 6/2010 | Pintor | A61F 2/2418 623/1.26 |
| 2010/0168834 A1 * | 7/2010 | Ryan | A61F 2/95 623/1.11 |
| 2010/0174363 A1 | 7/2010 | Castro | |
| 2010/0198347 A1 | 8/2010 | Zakay et al. | |
| 2010/0274344 A1 | 10/2010 | Dusbabek et al. | |
| 2011/0015729 A1 | 1/2011 | Jimenez et al. | |
| 2011/0054596 A1 | 3/2011 | Taylor | |
| 2011/0137331 A1 | 6/2011 | Walsh et al. | |
| 2011/0160846 A1 | 6/2011 | Bishop et al. | |
| 2012/0123529 A1 | 5/2012 | Levi et al. | |

(56) References Cited

U.S. PATENT DOCUMENTS

| | | |
|---|---|---|
| 2012/0239142 A1 | 9/2012 | Liu et al. |
| 2013/0030519 A1 | 1/2013 | Tran et al. |
| 2013/0317598 A1 | 11/2013 | Rowe et al. |
| 2014/0296962 A1 | 10/2014 | Cartledge et al. |
| 2015/0272733 A1 | 10/2015 | Le et al. |
| 2017/0065415 A1 | 3/2017 | Rupp et al. |
| 2018/0153689 A1 | 6/2018 | Maimon et al. |
| 2018/0214669 A1* | 8/2018 | Davies ............. A61M 25/0136 |
| 2018/0344456 A1 | 12/2018 | Barash et al. |
| 2019/0083259 A1 | 3/2019 | Le et al. |

FOREIGN PATENT DOCUMENTS

| | | | |
|---|---|---|---|
| EP | 0592410 | A1 | 4/1994 |
| EP | 0850607 | A1 | 7/1998 |
| EP | 1796597 | A2 | 6/2007 |
| FR | 2815844 | A1 | 5/2002 |
| WO | 1991017720 | A1 | 11/1991 |
| WO | 1998029057 | A1 | 7/1998 |
| WO | 1999012483 | A1 | 3/1999 |
| WO | 2001049213 | A2 | 7/2001 |
| WO | 2001054625 | A1 | 8/2001 |
| WO | 2001076510 | A2 | 10/2001 |
| WO | 2002022054 | A1 | 3/2002 |
| WO | 2002036048 | A1 | 5/2002 |
| WO | 2002047575 | A2 | 6/2002 |
| WO | 2002060352 | A1 | 8/2002 |
| WO | 2003030776 | A2 | 4/2003 |
| WO | 2003047468 | A1 | 6/2003 |
| WO | 2004019825 | A1 | 3/2004 |
| WO | 2005084595 | A1 | 9/2005 |
| WO | 2005102015 | A2 | 11/2005 |
| WO | 2006032051 | A2 | 3/2006 |
| WO | 2006111391 | A1 | 10/2006 |
| WO | 2006138173 | A2 | 12/2006 |
| WO | 2007047488 | A2 | 4/2007 |
| WO | 2007067942 | A1 | 6/2007 |
| WO | 2010121076 | A2 | 10/2010 |

* cited by examiner

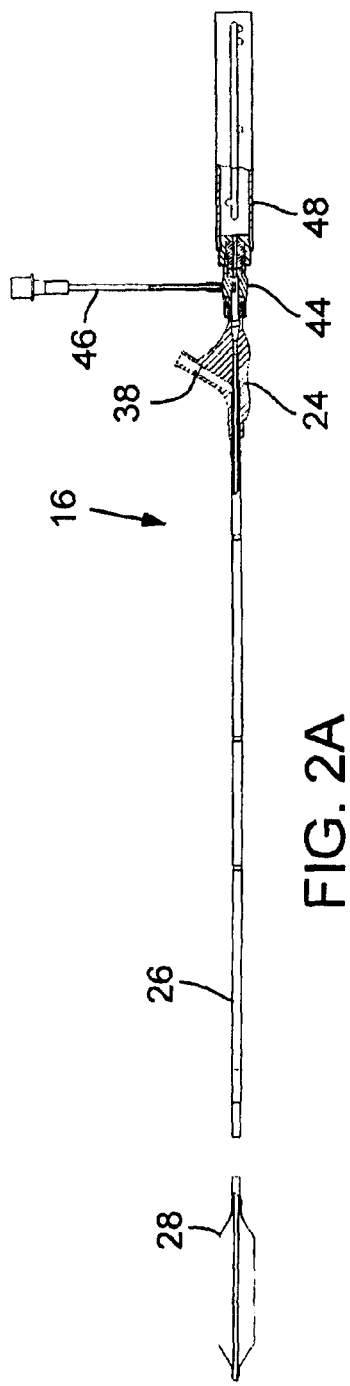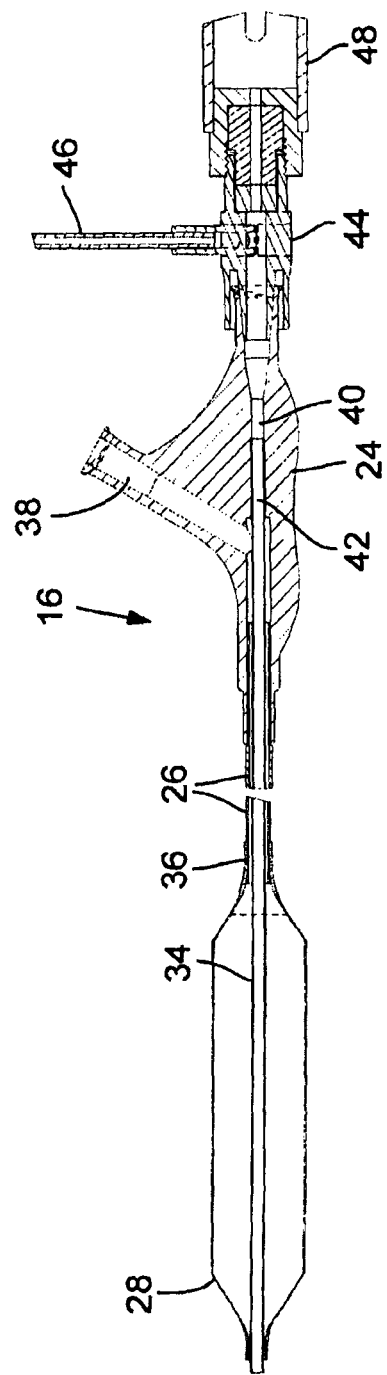
FIG. 2A
FIG. 2B

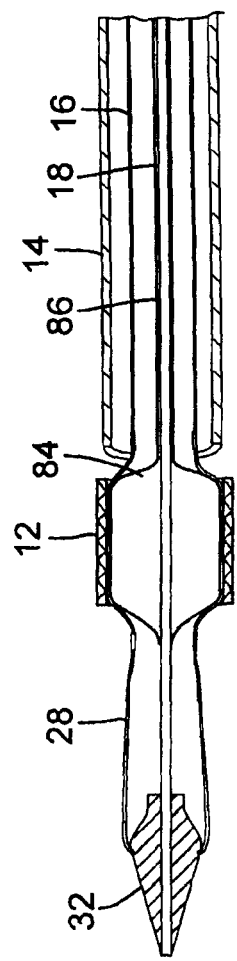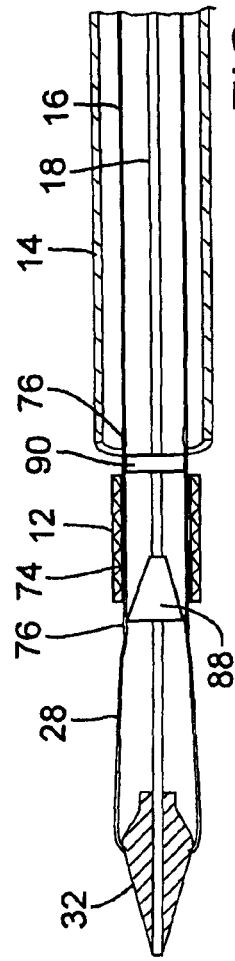

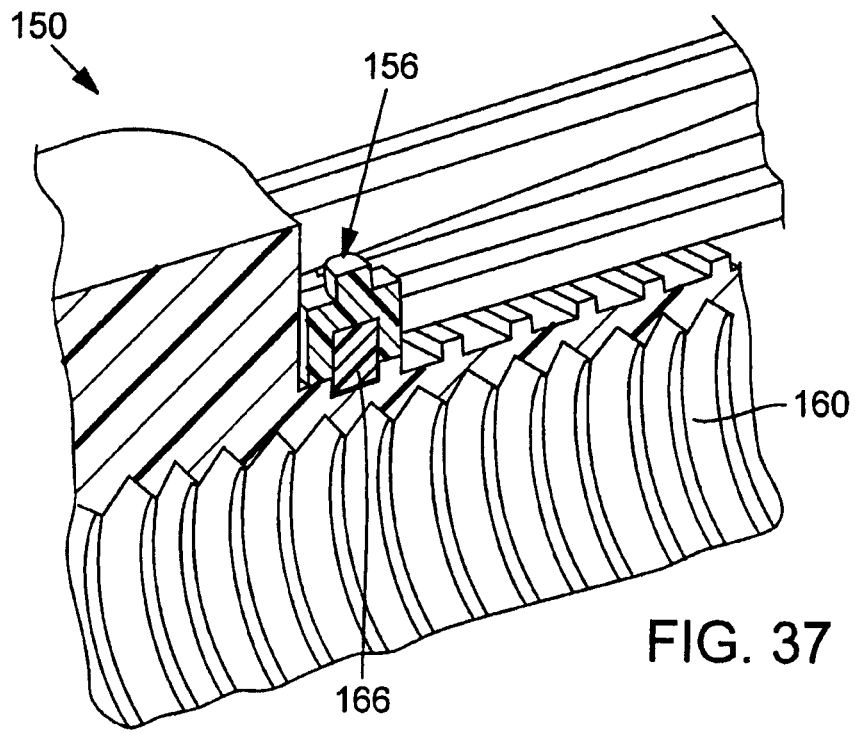
FIG. 37
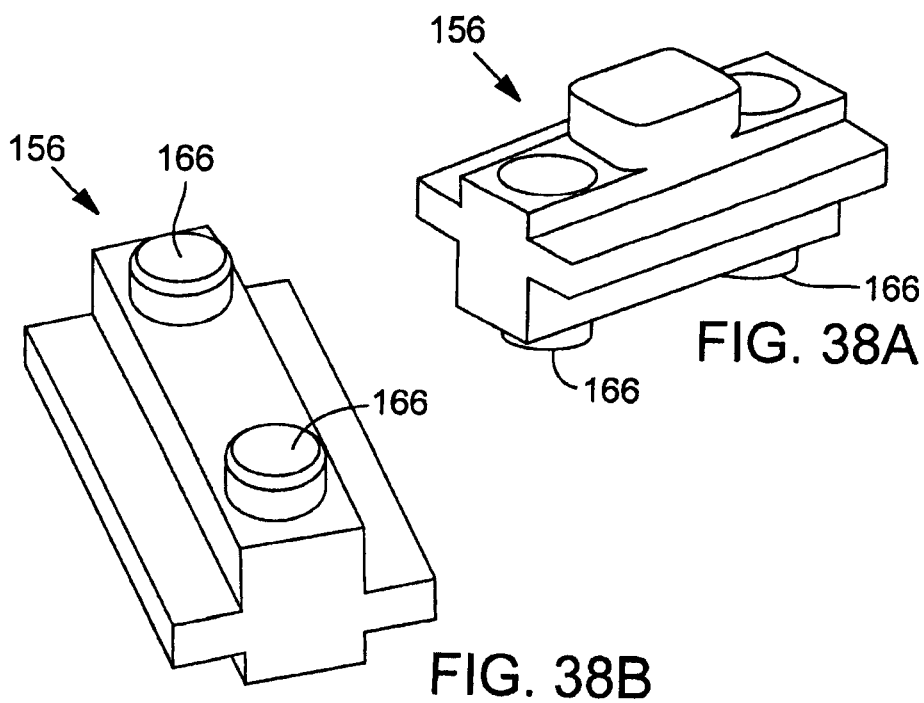
FIG. 38A
FIG. 38B

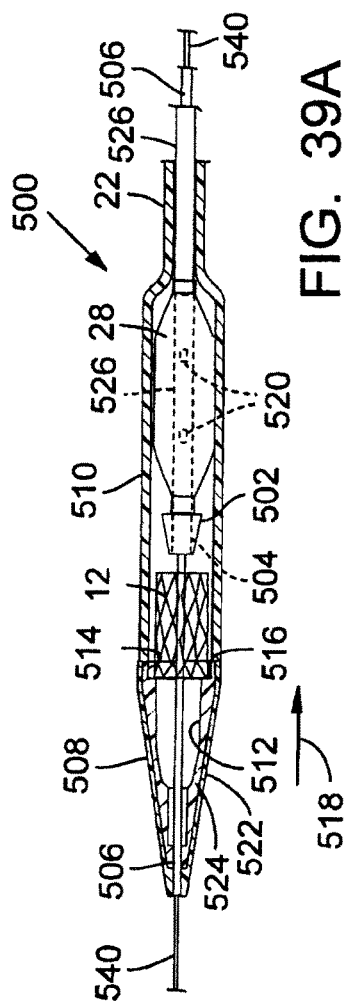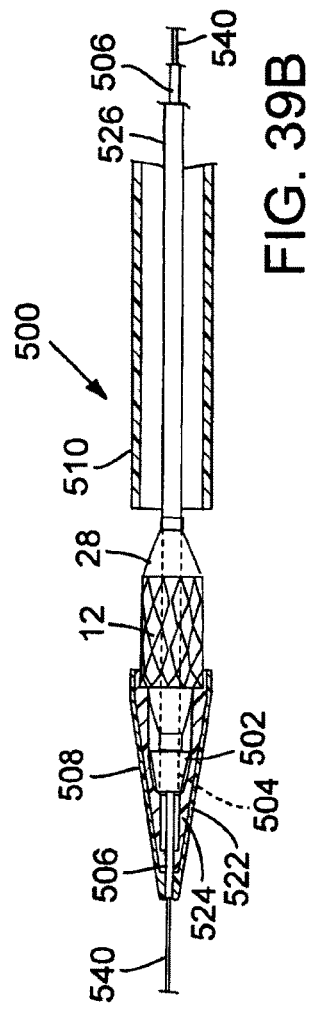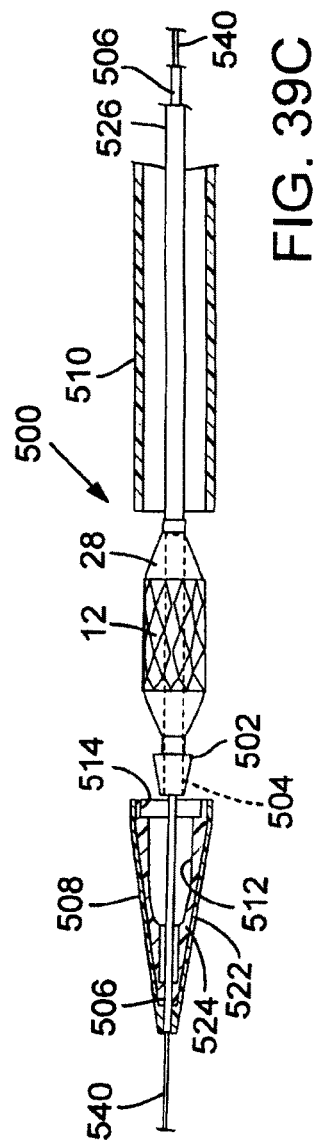

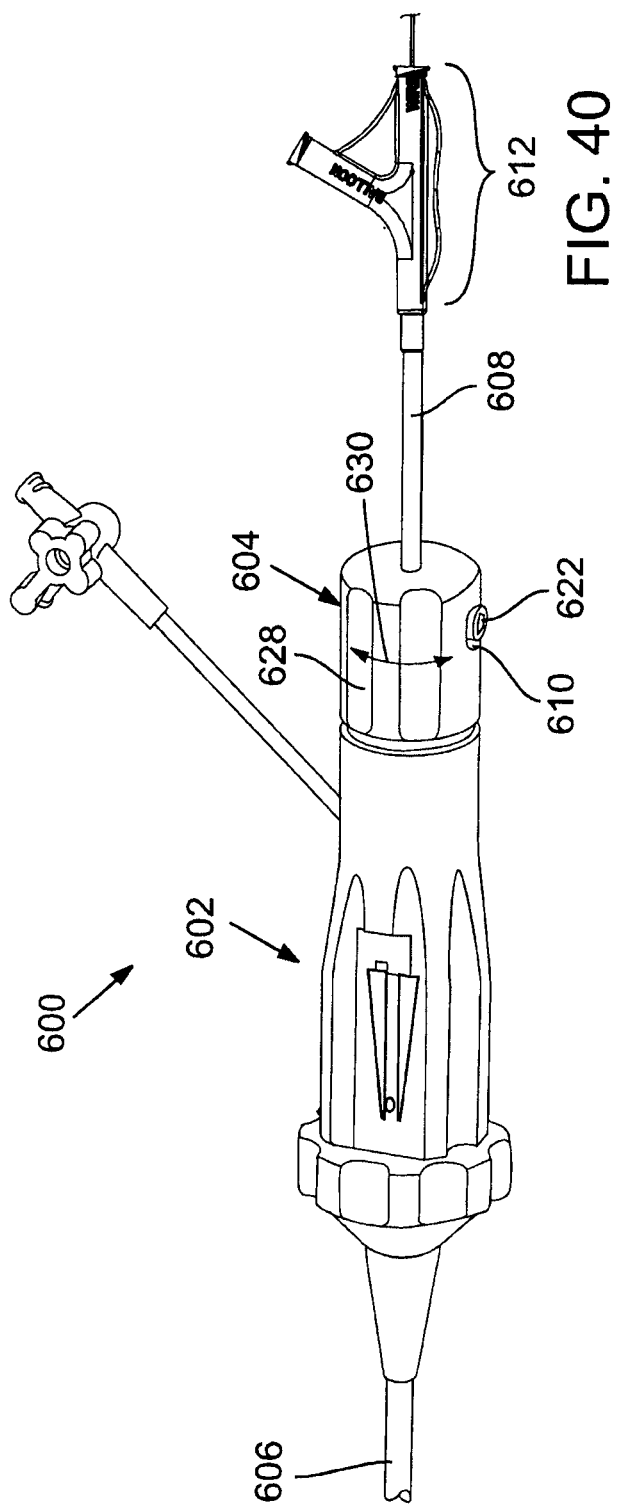
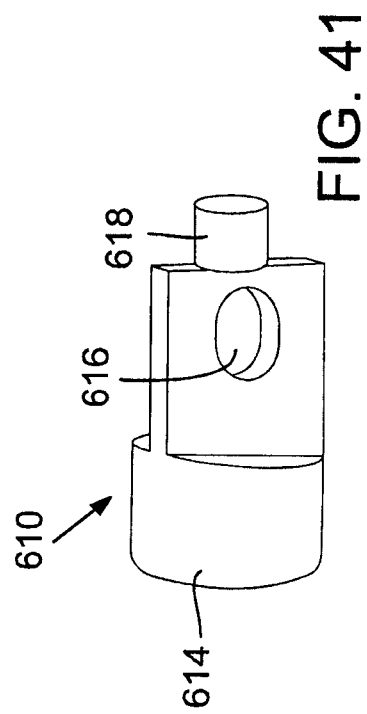
FIG. 40
FIG. 41

LOW PROFILE DELIVERY SYSTEM FOR TRANSCATHETER HEART VALVE

CROSS REFERENCE TO RELATED APPLICATIONS

This application is a continuation of U.S. patent application Ser. No. 14/736,117, filed Jun. 10, 2015, which is a continuation of U.S. patent application Ser. No. 12/247,846, filed Oct. 8, 2008, now U.S. Pat. No. 9,061,119, which claims the benefit of U.S. Provisional Application Nos. 61/083,117, filed Jul. 23, 2008, and 61/052,009, filed May 9, 2008. Each related application is incorporated by reference herein.

FIELD

The present invention relates to implantable devices. More particularly, the present invention relates to devices and methods for implantation of a prosthetic heart valve.

BACKGROUND

A transcatheter heart valve (THV) is a prosthetic heart valve which is configured to be implanted by a catheterization technique. One type of THV has been developed by Edwards Lifesciences of Irvine, Calif. and is described in U.S. Pat. No. 6,730,118, which is herein incorporated by reference in its entirety. The THV described in the '118 patent is primarily configured for replacing the function of a stenotic aortic valve in a human heart. An important feature of the THV is the ability to be implanted within the stenotic region of the native aortic valve. After implantation, the THV holds open the leaflets of the native aortic valve open and utilizes the native valve annulus as an attachment means for the THV.

An important design parameter of the THV is the diameter of the folded or crimped profile. The diameter of the crimped profile is important because it directly influences the physician's ability to advance the THV through the femoral artery or vein. More particularly, a smaller profile allows for treatment of a wider population of patients, with enhanced safety.

SUMMARY

Traditionally, the THV is crimped directly onto a balloon of a balloon catheter and the crimped THV and balloon are navigated through the patient's vasculature to the implantation site. Because of the thickness of the balloon material, the valve cannot be crimped to its smaller possible profile. In certain embodiments disclosed below, the balloon is positioned either distal or proximal to the crimped THV. This allows the THV to be crimped to a smaller diameter. After the THV is advanced through narrow portions in a patient's vasculature (for example, the iliac artery which is typically the narrowest portion of the relevant vasculature), the THV is placed onto the balloon. If the THV has not yet been advanced to the treatment site when the balloon member is repositioned underneath the THV, then the THV can then be advanced further to the treatment site and the balloon can be inflated to radially expand the THV within the native heart valve.

Advantageously, certain embodiments allow the THV to be crimped to a much smaller diameter and thereby overcome the primary shortcoming associated with THV deployment.

In one embodiment, an apparatus for delivering a prosthetic valve through the vasculature of a patient is disclosed. The apparatus comprises a main catheter, a balloon catheter, and a valve carrying member. The main catheter comprises an elongated shaft. The balloon catheter comprises an elongated shaft and a balloon connected to a distal end portion of the shaft. The shaft of the balloon catheter is capable of moving longitudinally within the shaft of the main catheter. The valve carrying member has a mounting surface for receiving a crimped valve for insertion into the vasculature of the patient. The balloon is positioned distal or proximal to the mounting surface and the balloon is configured to be movable relative to the mounting surface, or vice versa, to position the balloon at a location extending through the crimped valve after the valve is inserted into the patient's vasculature.

In specific implementations, the apparatus further comprises a nose piece and the valve carrying member extends between a proximal end of the nose piece and a distal end of the shaft of the main catheter.

In specific implementations, the valve carrying member comprises two or more strip members, with the strip members attached to the proximal end of the nose piece and the distal end of the shaft of the main catheter. In other specific implementations, the strip members are formed of a polymer material. In other specific implementations, the strip members are attached to an inside surface of the nose piece and an inside surface of the distal end of the shaft of the main catheter. In other specific implementations, the strip members comprise four polymer strips.

In specific implementations, a proximal end of the nose piece comprises one or more slits and the distal end of the shaft of the main catheter comprises one or more slits. In other specific implementations, the distal end of the shaft of the main catheter further comprises a flex adapter disposed at the location of the slits, with the flex adaptor having two or more fingers that are configured to maintain the slits in a radially expanded position in the absence of an inwardly directed force.

In specific implementations, the nose piece further comprises a polymer jacket surrounding at least a portion of the slits on the nose piece. In other specific implementations, the one or more strip members are positioned between the slits on the proximal end of the nose piece and the distal end of the shaft of the main catheter.

In specific implementations, the valve carrying member comprises an elongated shaft that extends coaxially with respect to the shaft of the main catheter. In other specific implementations, the shaft of the valve carrying member has a distal end portion that extends beyond the distal end of the shaft of the main catheter. The distal end portion of the shaft of the valve carrying member can comprise the mounting surface of the valve carrying member.

In specific implementations, the prosthetic valve is connected to the distal end of the shaft of the main catheter using a temporary connecting device. In other specific implementations, the temporary connecting device can comprise suture connected to the valve and a wire that is connected to the shaft of the main catheter and the suture. In other specific implementations, the shaft of the valve carrying member comprises a Nitinol braid or a polymer braid.

In specific implementations, the apparatus further comprises a nose piece, and the shaft of the valve carrying member extends between a proximal end of the nose piece and a distal end of the shaft of the main catheter. In other specific implementations, the distal end of the shaft of the valve carrying member is attached to an inside surface of the nose piece, and a portion of the shaft of the valve carrying member is disposed within the shaft of the main catheter.

In another embodiment, an apparatus for delivering a prosthetic valve through the vasculature of a patient is disclosed. The apparatus comprises a main catheter and a balloon catheter. The main catheter comprises an elongated shaft. The balloon catheter comprises an elongated shaft, a balloon connected to a distal end portion of the shaft, and an extension portion. The balloon catheter is capable of moving longitudinally within the shaft of the main catheter. The extension portion of the balloon catheter is located between the balloon and the elongated shaft and is configured to receive a prosthetic valve in a crimped state on an outer surface of the extension portion.

In specific implementations, the extension portion of the balloon catheter is formed of the same material as the balloon. In other specific implementations, the apparatus further comprises a nose piece with a distal portion of the balloon is attached to the nose piece. The distal portion of the balloon can be attached at approximately the mid-point of the nose piece. In addition, the nose piece can be configured to move relative to the crimped prosthetic valve, so that the nose piece can be moved adjacent to the crimped prosthetic valve while the crimped prosthetic valve is in the vasculature of the patient. The nose piece can have a substantially hourglass shape with a proximal concave portion, wherein the proximal concave portion of the nose piece is configured to receive at least a portion of the balloon when the nosepiece is moved adjacent to the crimped prosthetic valve.

In other specific implementations, the apparatus further comprises an expansion member that is disposed beneath the extension portion of the balloon catheter. The balloon and the expansion member are both configured to expand to a respective maximum expansion diameter, with the maximum expansion diameter of the balloon being greater than that of the expansion member. In other specific implementations, a dilator is disposed at a distal end of the extension portion, the dilator being configured to partially expand the crimped valve when the dilator is moved relative to the crimped valve. In other specific implementations, a stopper is disposed at a proximal end of the extension portion, the stopper being configured to resist movement of the crimped valve on the extension portion.

In another embodiment, a method of implanting a prosthetic valve at an implantation site in a patient's body is disclosed. The method comprises providing a delivery apparatus that comprises a main catheter that has an elongated shaft, a balloon catheter that has an elongated shaft and a balloon connected to a distal end portion of the shaft, and a valve carrying member. The valve is crimped to a smaller profile on a mounting surface of the valve carrying member. The valve and the delivery apparatus are inserted into the vasculature of the patient's body via an introducer sheath. The valve is mounted on the balloon after the valve passes through the introducer sheath. The valve is deployed at the implantation site by expanding the balloon.

In specific implementations, the method further comprises advancing the valve to the implantation site, wherein the act of mounting the valve on the balloon occurs after the valve passes through the introducer sheath but before advancing the valve to the implantation site.

In specific embodiments, the balloon is positioned proximal to the mounting surface during the act of crimping the valve, and the act of mounting the valve on the balloon comprises moving the balloon distally so that balloon is positioned underneath the crimped valve. In other specific implementations, the balloon is positioned distal to the mounting surface during the act of crimping the valve, and the act of mounting the valve on the balloon comprises moving the balloon proximally so that balloon is positioned underneath the crimped valve.

In specific implementations, the delivery apparatus further comprises a nose piece and the valve carrying member extends between a proximal end of the nose piece and a distal end of the shaft of the main catheter. In other specific implementations, the method further comprises securing the prosthetic valve to a distal end of the shaft of the main catheter using a temporary connection device. In other specific implementations, the method further comprises releasing the valve from the main catheter shaft after mounting the valve on the balloon.

In another embodiment, a method of implanting a prosthetic valve at an implantation site in a patient's body is disclosed. The method comprises: (a) providing a delivery apparatus that comprises a main catheter that has an elongated shaft, and a balloon catheter that has an elongated shaft, a valve carrying member, and a balloon connected to a distal end portion of the shaft, the valve carrying member of the balloon catheter being located between the balloon and the elongated shaft; (b) crimping the valve to a smaller profile on a mounting surface of the valve carrying member; (c) maneuvering the crimped valve through an introducer sheath into the vasculature of the patient's body; (d) adjusting the balloon's position relative to the crimped valve so that the balloon is positioned underneath the crimped valve; and (e) deploying the valve at the implantation site by expanding the balloon.

In specific implementations, the method further comprises partially expanding the valve by expanding an expansion member prior to adjusting the balloon's position relative to the valve.

In another embodiment, a method of implanting a prosthetic valve at an implantation site in a patient's body is disclosed. The method comprises: placing the valve in a crimped state on a distal end portion of an elongated delivery apparatus; inserting the crimped valve into the patient's body; subsequent to the act of inserting the crimped valve into the patient's body, moving the crimped valve onto an inflatable balloon on the distal end portion of the delivery apparatus; and deploying the valve at the implantation site by inflating the balloon.

In another embodiment, an apparatus for advancing a catheter through to an introducer sheath is disclosed. The apparatus comprises a retaining member and a drive member. The retaining member is configured to hold the introducer sheath in place relative to the apparatus. The drive member is operable to engage and drive the catheter through the introducer sheath.

In specific implementations, the drive member comprises a rotatable member and a first gear member. The first gear member comprises an engagement surface that is configured to frictionally engage an outside surface of the catheter. Rotating the rotatable member causes the first gear member to rotate and drive the catheter in a longitudinal direction relative to the introducer sheath.

In other specific implementations, the apparatus further comprises a second gear member. The second gear member also has an engagement surface that is configured to frictionally engage the outside surface of the catheter. In other specific implementations, both the first and second gear members have teeth, and when the first gear member rotates, the teeth of the first gear member engage the teeth of the second gear member so that the second gear member also rotates and drives the catheter in the longitudinal direction relative to the introducer sheath.

In other specific implementations, at least a portion of the engagement surface of the first gear member is coated with an elastomeric material. In other specific implementations, the first gear member comprises two parallel o-ring members.

In another embodiment, a method of advancing a catheter through an introducer sheath is disclosed. The method comprises providing an advancement apparatus having a drive member and a retaining member. The retaining member is configured to hold the introducer sheath in place relative to the advancement apparatus. The method further comprises securing the retaining member to the introducer sheath; and manually driving the drive member so that the drive member engages and drives the catheter through the introducer sheath.

In specific implementations, the drive member comprises a rotatable member and a first gear member, the first gear member comprising an engagement surface that is configured to frictionally engage an outside surface of the catheter, and the act of manually driving the drive member comprises rotating the rotatable member to cause the first gear member to rotate and drive the catheter in a longitudinal direction relative to the introducer sheath.

In another embodiment, an apparatus for indicating flex of a distal end of a catheter is disclosed. The apparatus comprises an elongated shaft; at least one wire connected to a distal end portion of the elongated shaft; a handle portion comprising a flex activating member, the flex activating member being coupled to the at least one wire such that adjustment of the flex activating member causes the distal end portion of the shaft to flex; and a flex indicating member. Adjustment of the flex activating member causes the flex indicating member to move relative to the handle to indicate an amount of flex of the distal end portion of the shaft.

In specific implementations, the flex activating member comprises a rotatable member. In other specific implementations, the handle portion comprises a slot for receiving at least a portion of the flex indicating member. In other specific implementations, the rotatable member includes an internally threaded surface portion and an externally threaded surface portion. The internally threaded surface portion is configured to receiving a slide member connected to the at least one wire, and the externally threaded surface portion is configured to receive an extending portion of the flex indicating member. In other specific implementations, rotating the rotatable member causes the slide member to move along the internally threaded surface portion and the movement of the slide member along the internally threaded surface portion changes the amount of flex of the distal end portion of the shaft. The rotation of the rotatable member causes the flex indicating member to move longitudinally and change its position within the slot of the handle portion and the position of the flex indicating member within the slot indicates the amount of flex of the distal end portion of the shaft.

In another embodiment, a method for manipulating a delivery apparatus through the vasculature of a patient is disclosed. The method comprises providing a delivery apparatus having an elongated shaft, a flex indicating member, and a handle portion, the handle portion comprising a flex activating member. The method further comprises manipulating the flex activating member to cause a distal end portion of the shaft to flex and to cause the flex indicating member to move relative to the handle portion. The method further comprises determining an amount of flex of the distal end portion of the shaft by observing a position of the flex indicating member relative to the handle portion.

In another embodiment, an apparatus for delivering a prosthetic valve through the vasculature of a patient can comprise a main catheter, a balloon catheter and a nose piece. The main catheter can comprise an elongated shaft. The balloon catheter can comprise an elongated shaft and a balloon connected to a distal end portion of the shaft. The shaft of the balloon catheter can be capable of moving longitudinally within the shaft of the main catheter. The nose piece can be disposed at a distal end of the main catheter and can comprise a balloon.

In another embodiment, an apparatus can include a main catheter comprising an elongated shaft, a balloon catheter comprising an elongated shaft and a balloon connected to a distal end portion of the shaft, and an adjustment device. The shaft of the balloon catheter can be capable of moving longitudinally within the shaft of the main catheter. The adjustment device can have a first portion and a second portion, the first and second portions being coupled together and being configured to rotate relative to each other to move from a first configuration to a second configuration. The relative longitudinal positions of the first and second portions in the first configuration can be different from the relative longitudinal positions of the first and second portion in the second configuration. The first portion can be coupled to the elongated shaft of the main catheter to restrict movement of the elongated shaft of the main catheter relative to the first portion, and the second portion can be coupled to the elongated shaft of the balloon catheter to restrict movement of the elongated shaft of the balloon catheter relative to the second portion, such that movement of the first and second portions between the first and second configurations is effective to move the shafts relative to each other.

In specific implementations, the first and second portions are further apart from each other in the second configuration than in the first configuration. In other implementations, the second portion further comprises a securing mechanism, the securing mechanism being configured to releasably secure the elongated shaft of the balloon catheter to the second portion.

In other implementations, the elongated shaft of the balloon catheter has at least one grooved section, the securing mechanism being biased to engage the grooved section to restrict movement of the elongated shaft of the balloon catheter relative to the second portion. In other specific implementations, the securing mechanism comprises an opening and a portion defining the opening, and the securing mechanism is disposed in the second portion so that the elongated shaft of the balloon catheter passes through the opening and the portion defining the opening is configured to engage with the grooved section.

In other specific implementations, each of the first and second portions has a threaded section, the threaded sections being configured to couple the first portion and second portion together. In other specific implementations, the adjustment device further comprises a rotatable member, the rotatable member being rotatable to move the first portion and the second portion from the first configuration to the second configuration. In other implementations, the apparatus further comprises a stop member, the stop member being configured to prevent the first and second portions from being separated from one another.

In another embodiment, a method for adjusting the relative positions of elongated shafts in a delivery apparatus is disclosed. The method comprising providing a delivery apparatus having an elongated shaft of a main catheter and an elongated shaft of a balloon catheter, the elongated shaft of the balloon catheter being at least partially disposed within the elongated shaft of the main catheter. An adjustment apparatus is provided, the adjustment apparatus having a first portion coupled to a second portion, the first and second portions being rotatable relative to each other. The elongated shaft of the main catheter is secured to the first portion. The elongated shaft of the balloon catheter is secured to the second portion. The first and second portions are rotated relative to each other, the rotation being effective to change the position of the second portion relative to the first portion such that the relative positions of the elongated shafts of the balloon catheter and the main catheter are adjusted.

In specific implementations, the balloon catheter comprises a balloon disposed at the distal end of the elongated shaft of the balloon catheter, and the delivery apparatus further comprises a valve disposed at a distal end of the delivery apparatus, and wherein the act of rotating the first and second portions relative to each other is effective to mount the valve on the balloon.

In specific implementations, the first and second portions comprise threaded portions that couple the first and second portions together, and the act of rotating the first and second portions relative to each other comprises rotating one or both of the first and second portions about the threaded portions.

The foregoing and other objects, features, and advantages of the invention will become more apparent from the following detailed description, which proceeds with reference to the accompanying figures.

BRIEF DESCRIPTION OF THE DRAWINGS

FIG. 2A is side view of the balloon catheter of the delivery apparatus of FIG. 1, shown partially in section.

FIG. 2B is an enlarged, cross-sectional view of the balloon catheter shown in FIG. 2A.

FIG. 19 is a side cross section view of an endovascular delivery apparatus for implanting a prosthetic valve.

FIG. 20 is a side cross section view of an endovascular delivery apparatus for implanting a prosthetic valve.

FIG. 37 is a partial perspective cross section view of a flex indicating device.

FIG. 38A is a top perspective view of an indicator pin for use with the flex indicating device shown in FIG. 31.

FIG. 38B is a bottom perspective view of an indicator pin for use with the flex indicating device shown in FIG. 31.

FIG. 39A is a side view of an endovascular delivery apparatus for implanting a prosthetic valve, shown partially in section.

FIG. 39B is a side view of an endovascular delivery apparatus for implanting a prosthetic valve, shown partially in section.

FIG. 39C is a side view of an endovascular delivery apparatus for implanting a prosthetic valve, shown partially in section.

FIG. 40 is a perspective view of an adjustment device for adjusting the relative positions of elongated catheter shafts.

FIG. 41 is a securing mechanism for use with the adjustment device of FIG. 40.

DETAILED DESCRIPTION

As used in this application and in the claims, the singular forms "a," "an," and "the" include the plural forms unless the context clearly dictates otherwise. Additionally, the term "includes" means "comprises." Further, the terms "coupled" generally means electrically, electromagnetically, and/or physically (e.g., mechanically or chemically) coupled or linked and does not exclude the presence of intermediate elements between the coupled items.

Figure 1:
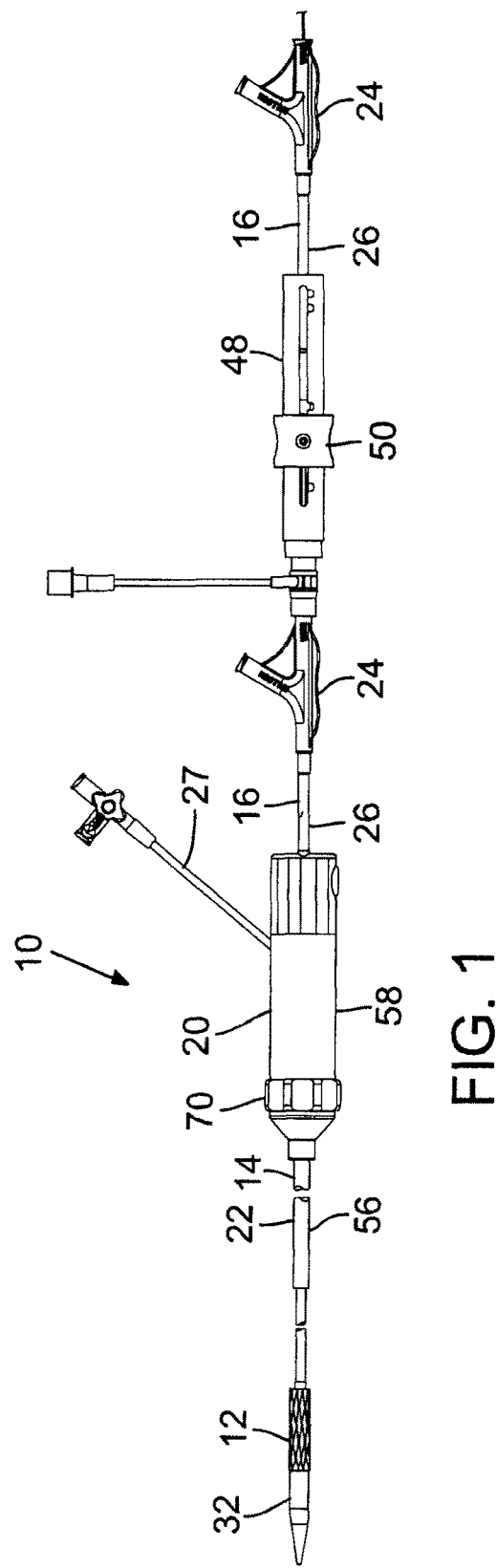
FIG. 1 is side view of an endovascular delivery apparatus for implanting a prosthetic valve.

FIG. 1 shows a delivery apparatus 10 adapted to deliver a prosthetic heart valve 12 (e.g., a prosthetic aortic valve) to a heart, according to one embodiment. The apparatus 10 generally includes a steerable guide catheter 14, and a balloon catheter 16 extending through the main catheter 14. The guide catheter can also be referred to as a flex catheter or a main catheter. The use of the term main catheter should be understood, however, to include flex or guide catheters, as well as other catheters that do not have the ability to flex or guide through a patient's vasculature.

The guide catheter 14 and the balloon catheter 16 in the illustrated embodiment are adapted to slide longitudinally relative to each other to facilitate delivery and positioning of valve 12 at an implantation site in a patient's body, as described in detail below.

The guide catheter 14 includes a handle portion 20 and an elongated guide tube, or shaft, 22 extending from handle portion 20. Balloon catheter 16 includes a proximal portion 24 adjacent handle portion 20 and an elongated shaft 26 that extends from proximal portion 24 and through handle portion 20 and guide tube 22. The handle portion 20 can include a side arm 27 having an internal passage which fluidly communicates with a lumen defined by the handle portion 20. An inflatable balloon 28 is mounted at the distal end of balloon catheter 16. In FIG. 1, valve 12 is positioned distally to balloon 28 (not shown in FIG. 1) and is shown in a crimped state, providing valve 12 with a reduced diameter for delivery to the heart via the patient's vasculature. Because valve 12 is crimped at a location different from the location of balloon 28 (e.g., in this embodiment valve 12 is crimped distal to balloon 28), valve 12 can be crimped to a lower profile than would be possible if valve 12 was crimped on top of balloon 28. This lower profile permits the surgeon to more easily navigate the delivery apparatus (including crimped valve 12) through a patient's vasculature to the treatment location. The lower profile of the crimped valve is particularly helpful when navigating through portions of the patient's vasculature which are particularly narrow, such as the iliac artery.

A nose piece 32 can be mounted at the distal end of the delivery apparatus 10 to facilitate advancement of the delivery apparatus 10 through the patient's vasculature to the implantation site. In some instances, it may be useful to have nose piece 32 connected to a separate elongated shaft so that nose piece 32 can move independently of other elements of delivery apparatus 10.

Nose piece 32 can be formed of a variety of materials, including various plastic materials. Alternatively, nose piece 32 can comprise an inflatable balloon member. When inflated, nose piece 32 can generally form a cone shape, such as is shown in FIG. 1. The inflation of nose piece 32, when nose piece 32 comprises a balloon member, can be achieved by having a lumen extend from a proximal end of the delivery apparatus to nose piece 32. A fluid pressurizing device can be in fluid contact with the lumen, and nose piece 32 can be inflated and deflated by the fluid pressurizing device. Nose piece 32 can be inflated to help track nose piece 32 through the vasculature of a patient and/or to provide a surface against which valve 12 can abut, which can help maintain the position of valve 12 on the delivery apparatus until deployment at the treatment site. For example, referring to FIG. 24 (discussed in more detail below), a balloon nose piece could be positioned distal to valve 12 and the balloon nose piece can be used to track the delivery system through a patient's vasculature. After deployment of valve 12 at the treatment site, nose piece 32 can be deflated, thereby reducing the profile of the delivery apparatus for withdrawal from the patient's vasculature.

As can be seen in FIGS. 2A and 2B, balloon catheter 16 in the illustrated configuration further includes an inner shaft 34 (FIG. 2B) that extends from proximal portion 24 and coaxially through outer shaft 26 and balloon 28. Balloon 28 can be supported on a distal end portion of inner shaft 34 that extends outwardly from outer shaft 26 with a proximal end portion 36 of the balloon secured to the distal end of outer shaft 26 (e.g., with a suitable adhesive). The outer diameter of inner shaft 34 is sized such that an annular space is defined between the inner and outer shafts along the entire length of the outer shaft. Proximal portion 24 of the balloon catheter can be formed with a fluid passageway 38 that is fluidly connectable to a fluid source (e.g., a water source) for inflating the balloon. Fluid passageway 38 is in fluid communication with the annular space between inner shaft 34 and outer shaft 26 such that fluid from the fluid source can flow through fluid passageway 38, through the space between the shafts, and into balloon 28 to inflate the same and deploy valve 12.

Proximal portion 24 also defines an inner lumen 40 that is in communication with a lumen 42 of inner shaft 34. The lumens 40, 42 in the illustrated embodiment can be sized to receive the shaft of a nose catheter, if desired. Balloon catheter 16 also can include a coupler 44 connected to proximal portion 24 and a tube 46 extending from the coupler. Tube 46 defines an internal passage which fluidly communicates with lumen 40. Balloon catheter 16 also can include a slide support 48 connected to the proximal end of coupler 44. The slide support 48 can support and cooperate with an adjustment ring 50 of a catheter (such as a nose catheter) to allow the catheter to be maintained at selected longitudinal positions relative to balloon catheter 16.

Inner shaft 34 and outer shaft 26 of the balloon catheter can be formed from any of various suitable materials, such as nylon, braided stainless steel wires, or a polyether block amide (commercially available as Pebax®). Shafts 26, 34 can have longitudinal sections formed from different materials in order to vary the flexibility of the shafts along their lengths. Inner shaft 34 can have an inner liner or layer formed of Teflon® to minimize sliding friction with nose catheter shaft 30.

Figure 3:
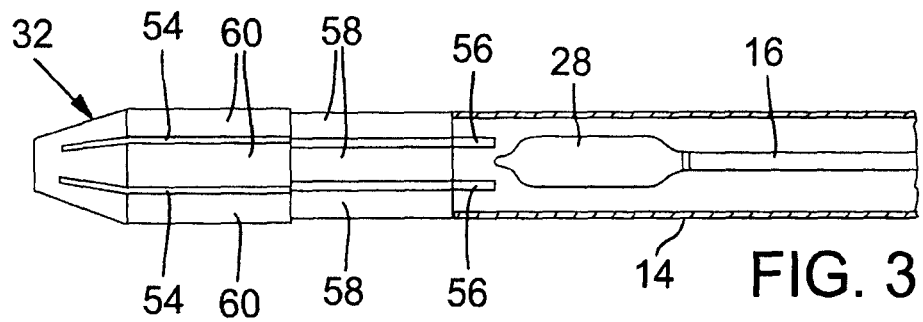
FIG. 3 is a side view of an endovascular delivery apparatus for implanting a prosthetic valve, shown partially in section.
Figure 4:
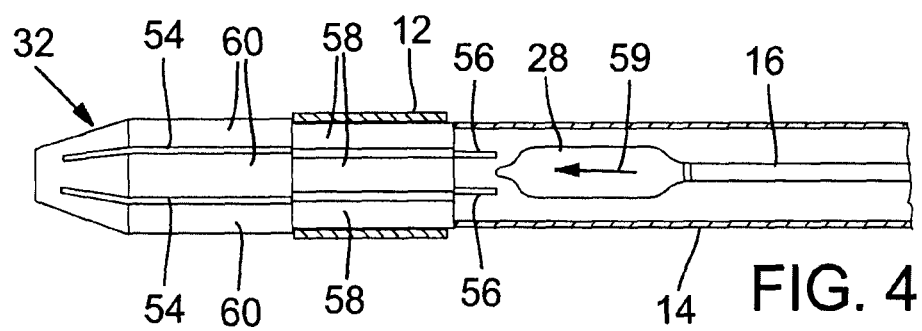
FIG. 4 is a side view of an endovascular delivery apparatus for implanting a prosthetic valve, shown partially in section.
Figure 5:
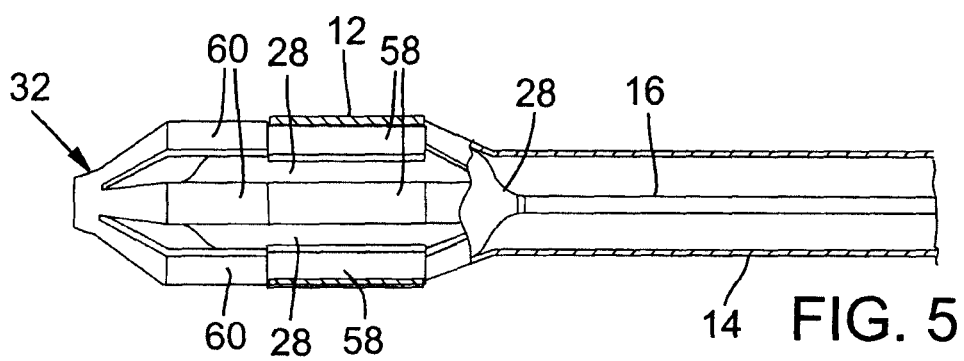
FIG. 5 is a side view of an endovascular delivery apparatus for implanting a prosthetic valve, shown partially in section.

FIGS. 3-5 illustrate an embodiment in which balloon 28 of balloon catheter 16 is initially positioned proximal to valve 12. FIG. 3 shows a delivery apparatus with support members 58 that are attached to nose piece 32 and a distal end of guide catheter 14. As discussed in more detail below, in this embodiment support members 58 (or valve carrying member) can take the form of polymer strips. For clarity, FIG. 3 shows the delivery apparatus without valve 12. FIG. 4 shows the delivery apparatus with valve 12 crimped on support members 58. FIG. 5 shows the delivery apparatus with valve 12 being expanded by balloon 28. In FIGS. 4 and 5, valve 12 is shown in section view so that the elements beneath valve 12 can be more easily understood.

Nose piece 32 in this embodiment is desirably a split nose piece having one or more slits 54 to accommodate expansion of balloon 28. Similarly, the distal end of guide catheter 14 is desirably formed with one or more slits 56 to accommodate expansion of balloon 28. The number of slits 54, 56 on the delivery apparatus 10 can vary. The nose piece 32 and the distal end of the guide catheter 14 desirably have about 1-8 slits each. In the present example, both the nose piece 32 and the distal end of the guide catheter 14 have four slits.

Support members 58 are attached to the proximal end of the nose piece 32 and the distal end of the guide catheter 14 Like the number of slits, the number of support members 58 can also vary. In the present example, there are four support members 58, with each support member (or strip) attaching to the nose piece 32 and the distal end of the guide catheter 14 between adjacent slits 54, 56. By having the same number of support members as there are slits in the nose piece and guide catheter, the support members 58 can be positioned intermediate the locations of the slits 54, 56.

In addition, if the number of slits and support members is the same, the slits and strips can be formed in a single cutting step. For example, an uncut cylindrical element can initially be attached to an uncut nose piece 32 and an uncut guide catheter 14. After attaching the cylindrical element to the nose piece 32 and the guide catheter 14, cuts can be made in each of the nose piece 32, guide catheter 14, and the cylindrical element (forming support members, or polymer strips, 58). In this manner, the cylindrical element can be cut into strips at the same time the slits in the nose piece and guide catheter are formed. In addition, by cutting the strips and slits in the same action, support members 58 will naturally align between slits 54, 56.

Alternatively, slits 54, 56 can be formed in nose piece 32 and guide catheter 14 before the strips are secured to the nose piece and guide catheter. Also, in another embodiment, the support members can be laser scored rather than formed into strips. Upon application of radial pressure (e.g., balloon expansion pressures), the laser-scored support member will break apart, thereby permitting expansion of the support member.

There need not be a one-to-one correspondence of support members 58 to slits 54, 56. Instead, if desired, there can be more support members 58 than slits 54, 56, or, alternatively, more slits 54, 56 than support members 58. Depending on the type of materials selected for the support members (or strips), it may be desirable to vary the form and shape of the support members. For example, it may be desirable to have more support members, fewer support members, smaller spaces (or gaps) between the support members, or wider spaces (or gaps) between the support members.

Support members 58 can be formed of a variety of materials. For example, support members 58 can be formed of such polymers as nylon, PET, PEEK, PE, Pebax, Urethane, and PVC. Support members 58 can be formed of a material that is non-compliant. Alternatively, support members 58 can be formed of materials that are flexible and/or stretchable so that when the balloon 28 is inflated, the support members can flex and/or stretch with the expansion of the balloon 28.

Support members 58 can be attached to inside or outside portions of nose piece 32 and the distal end of guide catheter 14. Support members 58, however, are desirably attached inside of nose piece 32 and guide catheter 14. In this manner, when valve 12 is crimped on support members 58, the proximal edge of nose piece 32 and the distal edge of guide catheter 14 can abut the opposite ends of the valve and form a natural barrier, thereby reducing the likelihood that valve 12 will slide longitudinally or move out of position between nose piece 32 and guide catheter 14. If support members 58 are attached on an outside portion of nose piece 32 and guide catheter 14, valve 12 will not be held in position by the ends of the nose piece and guide catheter. Accordingly, if support members 58 are attached to the outside portion of these elements, it may be desirable to further include a stopping mechanism (such as a raised portion or lip) at the area just outside of the location where the valve will seat on the support members to reduce the risk that valve 12 will slide out of position over the adjacent edges of nose piece 32 and guide catheter 14.

FIG. 4 shows valve 12 crimped on support members 58, with balloon 28 positioned proximally to valve 12. As discussed above, since balloon 28 is not positioned inside valve 12, valve 12 can be crimped to a smaller profile. Thus, the delivery apparatus can more easily navigate the narrowest portions of the patient's vasculature. After valve 12 advances through the narrowest portions of the patient's vasculature (e.g., the iliac artery), balloon 28 can be advanced distally, as indicated by arrow 59 in FIG. 4, by pushing balloon catheter 16 towards the nose piece 32 to position the balloon within valve 12 for valve deployment. Valve 12 can then be advanced further in the patient's vasculature to the treatment site. As can be seen in FIG. 5, the balloon 28 typically is longer than the valve so that when the balloon is positioned in the valve, a distal end portion of the balloon extends into nose piece 32 and a proximal end portion of the balloon remains in the distal end portion of the guide catheter.

Alternatively, valve 12 can be advanced completely through the vasculature to the treatment site in a position distal (as described in this embodiment) or proximal (as described in other embodiments below) to the location of balloon 28. Once valve 12 reaches the treatment site, the balloon can be moved into position underneath the valve for deployment. It should be understood that for each of the embodiments disclosed herein, the balloon can be repositioned within the valve at any time after passing through the narrow portions of the patient's vasculature, including immediately after passing through the introducer sheath, at the treatment site itself, or at some location in between.

FIG. 5 shows balloon 28 in an expanded state, with balloon 28 expanding valve 12. Slits 54, 56 allow nose piece 32 and guide catheter 14 to at least partially expand with balloon 28. The method and manner of inflating balloons is known and balloon 28 can be inflated in any known manner. Once valve 12 is expanded to the desired size, balloon 28 can be deflated, and balloon catheter 14 and the other elements of the delivery apparatus can be retracted from the patient's vasculature.

Alternatively, instead of having one or more support members formed into strips, a single cylindrical member formed of an elastic material could be used. If the cylindrical member is formed of a material of sufficient elasticity to expand to accommodate the diameter of an expanded balloon, the cylindrical member can be formed in a single or unitary piece of material, which is not cut into multiple strips as discussed above.

Figure 6:
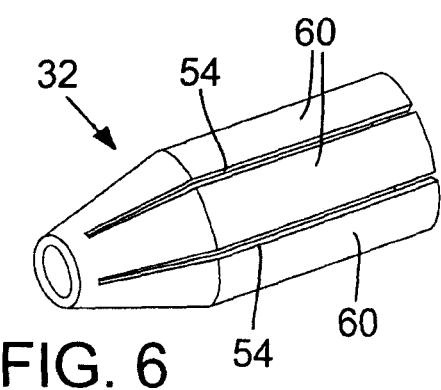
FIG. 6 is a perspective view of a nose piece for use with an endovascular delivery apparatus for implanting a prosthetic valve.

FIG. 6 shows nose piece 32 formed with slits 54 to accommodate expansion of the distal end portion of balloon 28. Slits 54 define flaps 60 that can flex radially outward from each other to form a larger opening. Accordingly, during expansion of the balloon, if a portion of the distal end of the balloon 28 is positioned under a proximal portion of the nose piece, the balloon can still be fully inflated since the proximal portion of the nose piece 32 can expand to accommodate the expanded balloon.

Figure 7:
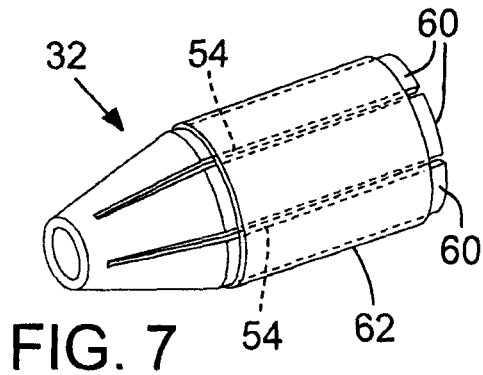
FIG. 7 is a perspective view of a nose piece for use with an endovascular delivery apparatus for implanting a prosthetic valve.
Figure 8:
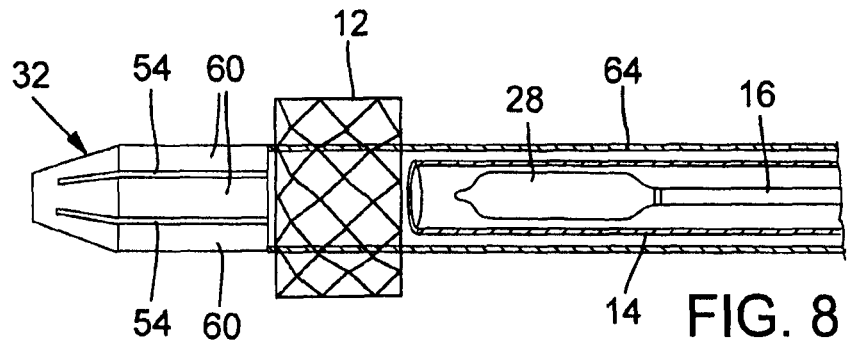
FIG. 8 is a side view of an endovascular delivery apparatus for implanting a prosthetic valve, shown partially in section.

FIG. 7 shows another embodiment of a nose piece 32. It may be desirable to position a jacket 62 over at least a portion of flaps 60. Jacket 62 is desirably formed of an elastic, flexible polymer that can expand when a balloon inflates forcing flaps 60 radially outward. Once the balloon is deflated, however, the elastic properties of jacket 62 cause flaps 60 to return to their normal (closed) position. Jacket 62 can be formed of a variety of elastic materials, including, for example, urethane, silicone, and latex. Alternatively, instead of wrapping a polymer around at least a portion of flaps 60, the nose piece 32, or at least a portion of nose piece 32, can be dipped into an elastic material (such as those discussed above) to form the jacket 62. In this manner, jacket 62 can be formed by coating the elastic material on the nose piece 32 such that the coating acts in substantially the same manner as the polymer wrap described above.

FIGS. 8-12 show another embodiment of a delivery apparatus for delivering a valve 12 to a treatment site using a valve carrying member. As discussed in more detail below, in this embodiment the valve carrying member can take the form of an outer sleeve. Outer sleeve 64 extends over the guide catheter 14 from a distal end (shown in FIG. 8) to a proximal end near the proximal end of the guide catheter 14 and can be independently manipulated by a handle portion (not shown). The outer sleeve 64 can be manipulated in a manner that is the same or similar to the manipulation that the guide catheter is capable of, as discussed above.

Outer sleeve 64 is attached to nose piece 32. Outer sleeve 64 can be attached to an inside or outside portion of nose piece 32; however, it is desirably attached to an inside portion so that the proximal edge of the nose piece 32 can abut and limit movement of the crimped valve 12 in the distal direction. Outer sleeve 64 is desirably formed of Nitinol, stainless steel, or a polymer such as nylon, PET, PEEK, PE, Pebax, Urethane, and PVC.

Figure 9:
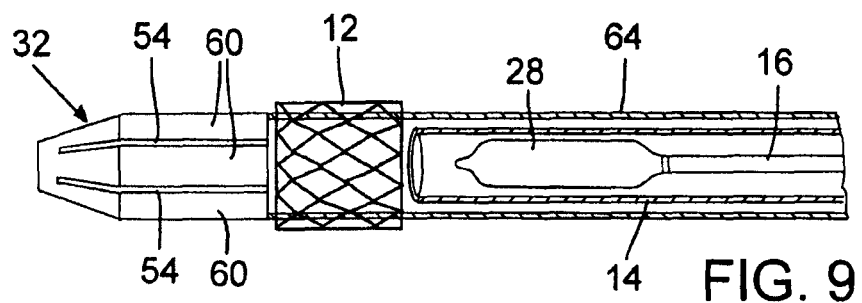
FIG. 9 is a side view of an endovascular delivery apparatus for implanting a prosthetic valve, shown partially in section.

Valve 12 is initially crimped onto the distal end portion of outer sleeve 64 as shown in FIG. 9. Desirably, outer sleeve 64 is formed as a braid or with laser cuts, so that outer sleeve 64 can expand radially during implantation of the valve 12 at the treatment site. If desired, outer sleeve 64 can be formed with only a portion of it braided or laser cut. The braided or cut portion should include at least the portion of outer sleeve 64 where the valve 12 is crimped onto outer sleeve 64, so that the portion of the outer sleeve 64 that extends through valve 12 can be expanded along with valve 12.

Figure 10:
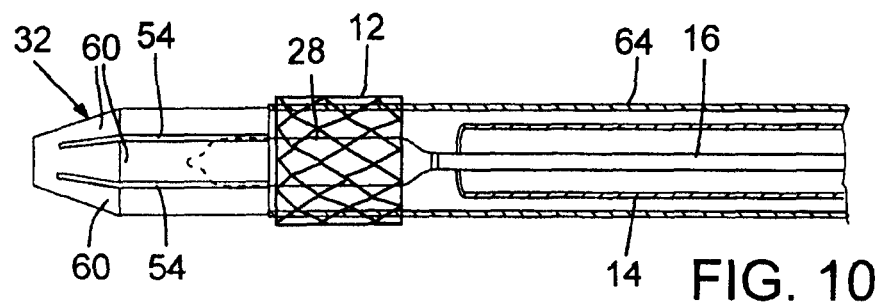
FIG. 10 is a side view of an endovascular delivery apparatus for implanting a prosthetic valve, shown partially in section.
Figure 11:
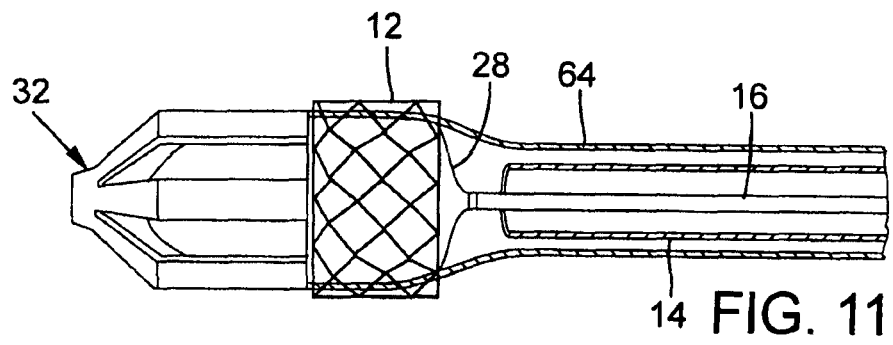
FIG. 11 is a side view of an endovascular delivery apparatus for implanting a prosthetic valve, shown partially in section.
Figure 12:
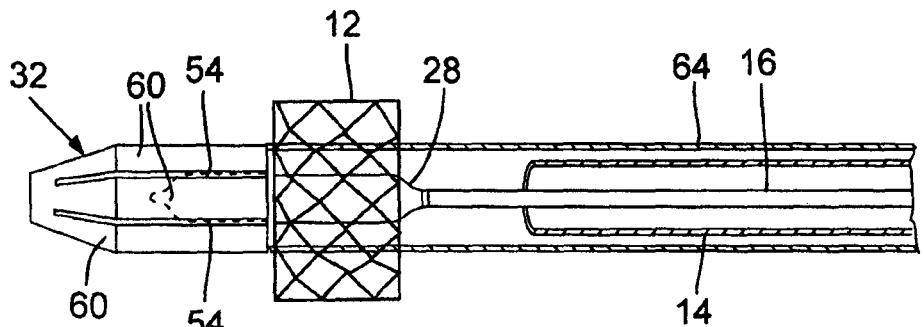
FIG. 12 is a side view of an endovascular delivery apparatus for implanting a prosthetic valve, shown partially in section.

After valve 12 is in position for deployment (or, if desired, sometime after the valve passes the narrowest portions of the patient's vasculature), balloon 28 can be moved distally relative to guide catheter 14 and positioned to extend through valve 12, as shown in FIG. 10. FIG. 11 shows balloon 28 in an expanded state. Once valve 12 is expanded to the desired diameter, balloon 28 can be deflated (as shown in FIG. 12) and the delivery apparatus can be retracted from the patient's vasculature.

Figure 13:
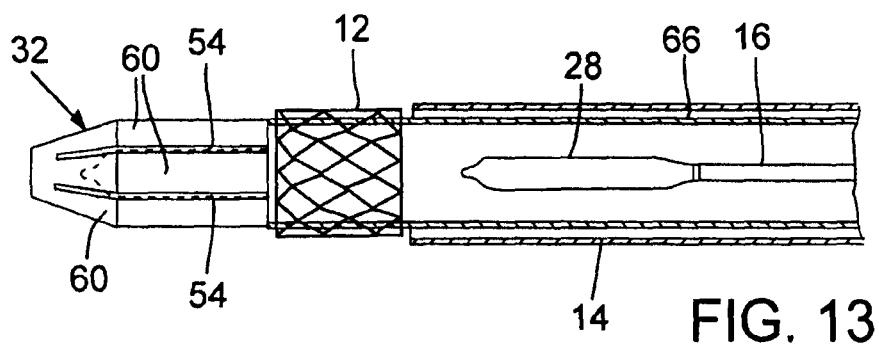
FIG. 13 is a side view of an endovascular delivery apparatus for implanting a prosthetic valve, shown partially in section.
Figure 14:
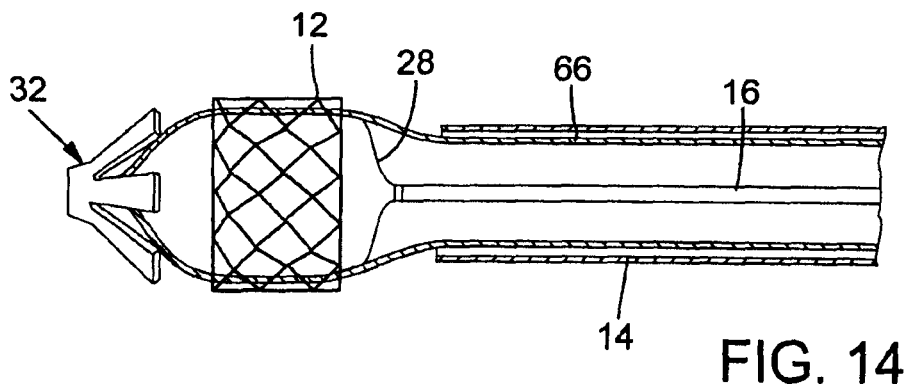
FIG. 14 is a side view of an endovascular delivery apparatus for implanting a prosthetic valve, shown partially in section.
Figure 15:
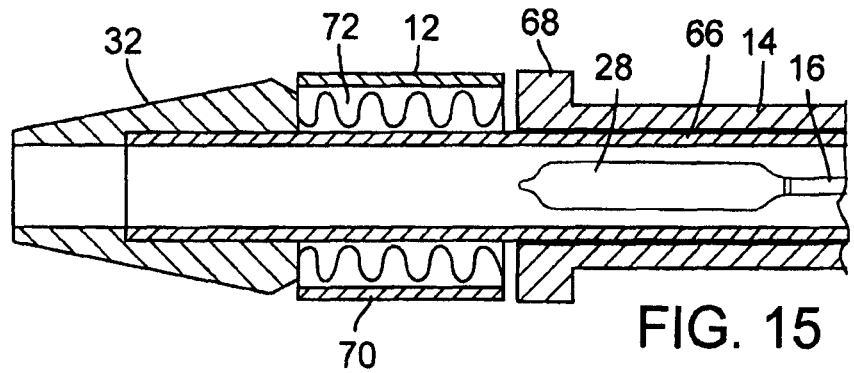
FIG. 15 is a side cross section view of an endovascular delivery apparatus for implanting a prosthetic valve.

FIGS. 13-15 show an embodiment where a valve 12 is crimped onto an inner sleeve 66. Referring to FIG. 13, inner sleeve 66 is similar to outer sleeve 64, except that it is positioned inside—instead of outside—of guide catheter 14. Inner sleeve 66 desirably extends the length of guide catheter 14 and can be independently manipulated at its proximal end to move inner sleeve 66 longitudinally relative to guide catheter 14. By positioning inner sleeve 66 inside of guide catheter 14, the distal edge of guide catheter 14 can abut the proximal end of crimped valve 12 and prevent valve 12 from moving or sliding out of position. In addition, as shown in FIG. 15, the distal end of guide catheter 14 can be formed with a lip 68 so that guide catheter 14 can seat better against the proximal end of valve 12.

It is also desirable to attach the distal end of the inner sleeve 66 to an inside portion of the proximal end of the nose piece 32. By attaching inner sleeve 66 to an inside portion of nose piece 32, valve 12 can be more securely held in position between nose piece 32 and guide catheter 14.

FIG. 14 shows balloon 28 in its expanded state after it has been advanced to a position extending through the portion of the inner sleeve 66 on which the valve is mounted. Inflating the balloon causes that portion of inner sleeve 66 and valve 12 to expand. Once valve 12 is expanded to the proper diameter, balloon 28 can be deflated and retracted as discussed in the other embodiments. FIG. 15 is a cross section view of the delivery apparatus. Valve 12 includes an outer frame portion 70 and an inner portion that includes leaflets 72. Valve 12 is positioned between nose piece 32 and the distal end of catheter 14, which can include a lip 68 to better mate with the frame portion 70 of valve 12.

The use of a braided or laser-cut outer or inner sleeve that is formed of a metal, such as Nitinol, also permits valve 12 to be repositioned after it has been partially expanded. In traditional delivery apparatuses, the valve is crimped onto a balloon. If the balloon is partially inflated and the surgeon observes that the valve is not properly positioned, it is very difficult to reposition the valve. First, the balloon must be deflated so that the orifice is not occluded for too long a period. Because expansion of a balloon occludes the orifice (such as the aortic valve), the period that the balloon can be expanded at the treatment site is relatively brief. Once the balloon is deflated, however, there is nothing that is holding the valve in position relative to the balloon. When using an inner or outer sleeve as discussed above, however, the inner or outer sleeve is expanded with the valve. Thus, the valve remains in position on the inner or outer sleeve. If the surgeon observes that the valve is not properly position, the surgeon can deflate the balloon and maneuver the valve by manipulating the position of the inner or outer sleeve. The metal sleeve can be collapsed down from the partially expanded state by any known method. For example, a stretching force can be applied to the metal sleeve to stretch or lengthen the metal sleeve so that the diameter of the sleeve is reduced. This can be achieved by applying forces at the proximal end of the metal sleeve or at the distal end of the metal sleeve using, for example, rigid wires.

Figure 16:
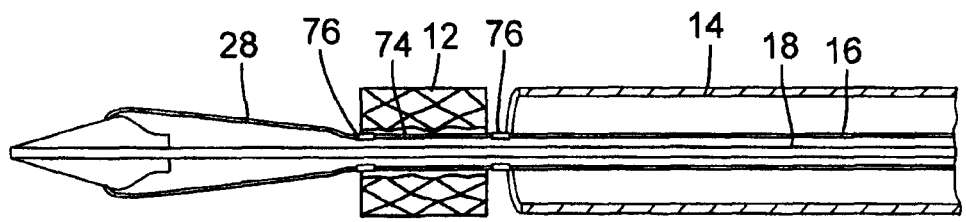
FIG. 16 is a side cross section view of an endovascular delivery apparatus for implanting a prosthetic valve.

FIG. 16 shows an embodiment in which a valve 12 is crimped onto a delivery apparatus proximal to a balloon 28 of a balloon catheter 16. Balloon catheter 16 includes an extension portion 74 that extends from a proximal end of balloon 28. The extension portion 74 can be formed of the same material as balloon 28 and can be an integral piece of balloon 28. Alternatively, extension portion 74 can be a separate material that is formed of the same or different material and which is bonded, welded, glued, or otherwise attached between balloon 28 and balloon catheter 16 at bond areas 76. The extension portion 74 desirably has a smaller cross section or profile than balloon 28, so that valve 12 can be crimped to a smaller profile on extension portion 74 than it can on balloon 28. Extension portion 74 can be formed of any suitable material, such as the polymers discussed above, which include nylon, PET, PEEK, PE, Pebax, Urethane, and PVC.

Figure 17:
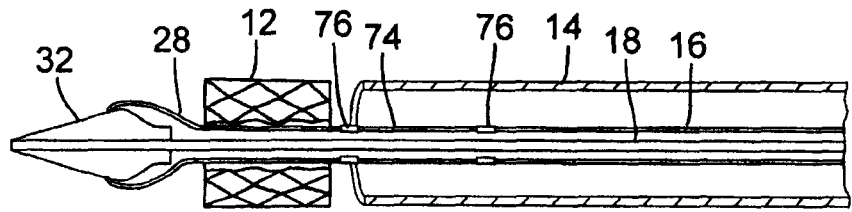
FIG. 17 is a side cross section view of an endovascular delivery apparatus for implanting a prosthetic valve.

Balloon 28 can be attached to a nose piece 32. Desirably, a distal portion of balloon 28 is attached to approximately the mid-point of the nose piece 32. Nose piece 32 can be useful to provide a more efficient tracking profile of the distal end of the delivery apparatus through a patient's vasculature. For example, the tapered shape of nose piece 32 as well as its more rigid structure (as compared to balloon 28) can function to make delivery of the valve through the vasculature more efficient. In particular, nose piece 32 can be substantially hourglass shaped, as shown in FIG. 16. By forming nose piece 32 with a proximal concave (tapered) portion as shown in FIG. 16, when the nose piece 32 is moved proximally to abut, or be adjacent to, the crimped valve (as shown in FIG. 17), the concave portion can receive at least a portion of the balloon. Thus, by moving the nose piece 32 so that it abuts the crimped valve, a portion of the balloon can be received in the concave portion, and a smooth, atraumatic profile can be achieved to facilitate tracking of the valve over the aortic arch and when crossing the stenotic valve.

Also, it may be desirable to include an elongated shaft attached to nose piece 32. This elongated shaft 18 can provide additional structure and support in guiding balloon catheter 16 through the patient's vasculature.

After valve 12 passes the narrowest portions of the patient's vasculature (or, if desired, at some later position including, for example, the point of deployment), balloon 28 can be pulled back (moved proximally) by retracting balloon catheter shaft 16 at its handle (not shown) to position the balloon within valve 12, as shown in FIG. 17. FIG. 17 shows balloon 28 in an unexpanded state. As described in more detail in other embodiments, when valve 12 is in position at the treatment site, valve 12 can be expanded to the desired diameter by inflating balloon 28, balloon 28 can be deflated with valve 12 secured by friction at the treatment site, and the delivery apparatus can be retracted from the patient's vasculature.

Figure 18:
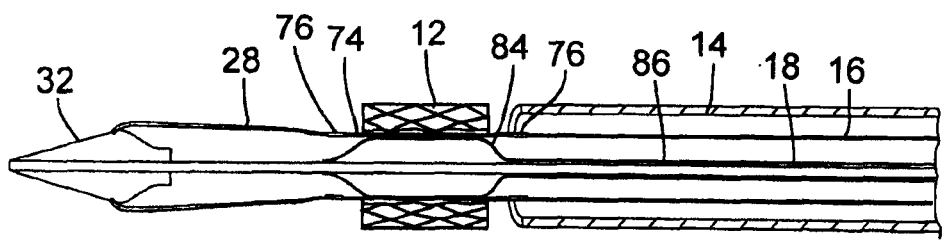
FIG. 18 is a side cross section view of an endovascular delivery apparatus for implanting a prosthetic valve.

If desired, the configuration of FIG. 18 could be achieved before insertion of the valve 12 into the vasculature of the patient. That is, the hourglass shape of nose piece 32 can provide a beneficial tracking profile, without regard to whether the configuration shown in FIG. 18 is achieved inside or outside of the patient's vasculature. However, as discussed in detail above, moving the apparatus into the configuration shown in FIG. 18 while in the patient's vasculature allows for a smaller insertion profile which is desirable to facilitate insertion of the valve into the patient's vasculature.

In addition, by providing an apparatus with a balloon distal to the valve, it is possible to inflate the balloon to perform valvuloplasty to open a stenotic heart valve, prior to moving the balloon in position to expand the valve. In such a procedure, the process of moving the balloon into position for expanding the valve would be the same as discussed herein, except that it would occur after (1) expanding the balloon to apply expansion forces to the stenotic heart valve and (2) deflating the balloon so that it can return to the state shown in FIG. 16.

FIG. 18 shows another embodiment where an expansion member (second smaller balloon 84) is positioned inside balloon 28 and valve 12 is crimped on top of the expansion member (second balloon 84). Because second balloon 84 is smaller in diameter than balloon 28, valve 12 can be crimped to a smaller diameter when crimped on second balloon 84 than when crimped on balloon 28.

Second balloon 84 can serve to hold valve 12 in place as the device is maneuvered through the patient's vasculature. In addition, second balloon 84 can be separately expandable so that second balloon 84 can partially expand valve 12 so that it is easier to move balloon 28 in position within valve 12 for deployment of the valve at the treatment site. Second balloon 84 can be attached to the end of a shaft 86. Shaft 86 has a lumen that can be in fluid connection with a fluid source and second balloon 84. Fluid can be transported through the lumen of shaft 86 and into second balloon 84 to cause second balloon 84 to inflate and at least partially expand valve 12. Referring to FIG. 19, second balloon 84 is shown in an inflated state, with valve 12 being partially expanded. After partially expanding valve 12, second balloon 84 can be deflated and balloon 28 can be pulled back (moved proximally) into position beneath the partially expanded valve 12. After balloon 28 is moved back into position extending through the partially expanded valve 12, valve 12 can then be expanded to the desired diameter by inflating balloon 28, balloon 28 can be deflated with valve 12 expanded in the desired position at the treatment site, and the delivery apparatus can be retracted from the patient's vasculature.

FIG. 20 is another embodiment of a delivery apparatus. Similar to the embodiment shown in FIGS. 16 and 17, balloon catheter 16 has an extension portion 74 that has a smaller diameter than balloon 28, so that valve 12 can be crimped to a smaller profile on extension portion 74 than it can on balloon 28. The extension portion 74 can be formed of the same material as balloon 28 and an integral piece of balloon 28. Alternatively, extension portion 74 can be a separate material that is formed of the same or different material and which is bonded, welded, glued, or otherwise attached between balloon 28 and balloon catheter 16 at bond areas 76. The apparatus shown in FIG. 20 also includes a dilator 88 and a stopper 90. Dilator 88 and stopper 90 can be attached to the inside surface of the extension portion 74 or to the outside surface of the shaft of nose catheter 18 (if a nose catheter is included). Dilator 88 and stopper 90 can both serve to hold the crimped valve 12 in position on extension portion 74.

Stopper 90 can be generally cylindrical in shape, with one or more openings passing through its center to accommodate the elongated shaft of the nose catheter and allow fluid to flow into the balloon. When extension portion 74 is pushed forward or pulled back relative to guide catheter 14, the thin extension portion is susceptible to buckling or bunching. Stopper 90 can reduce the buckling of the thin layer of material by adding structural strength to extension portion 74.

Figure 21A:
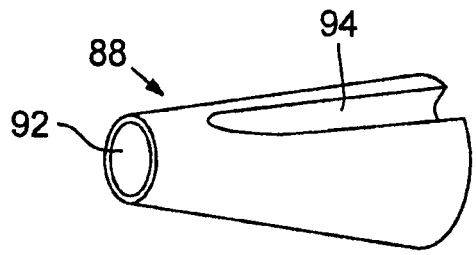
FIG. 21A is a perspective view of a dilator for use with an endovascular delivery apparatus for implanting a prosthetic valve.
Figure 21B:
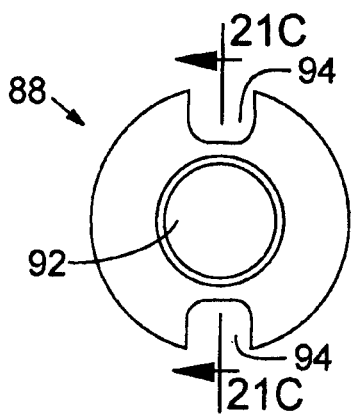
FIG. 21B is bottom view of a dilator for use with an endovascular delivery apparatus for implanting a prosthetic valve.
Figure 21C:
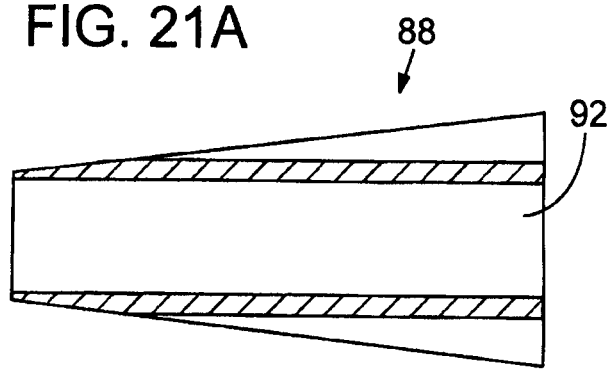
FIG. 21C is a cross section view of a dilator for use with an endovascular delivery apparatus for implanting a prosthetic valve, taken along line 21C-21C.
Figure 22A:
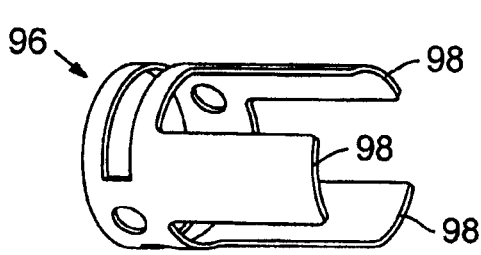
FIG. 22A is a perspective view of a flex tip for use with an endovascular delivery apparatus for implanting a prosthetic valve.
Figure 22B:
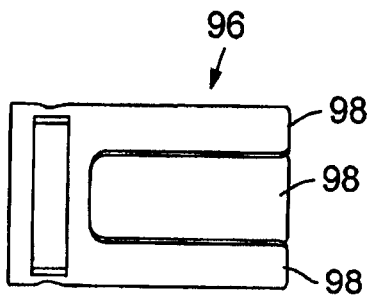
FIG. 22B is a side view of a flex tip for use with an endovascular delivery apparatus for implanting a prosthetic valve.
Figure 22C:
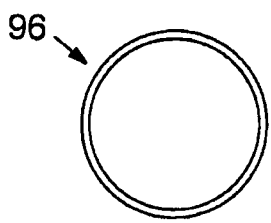
FIG. 22C is a top view of a flex tip for use with an endovascular delivery apparatus for implanting a prosthetic valve.
Figure 22D:
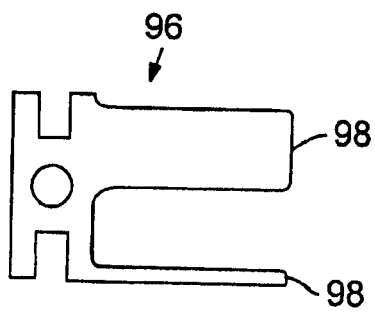
FIG. 22D is another side view of a flex tip for use with an endovascular delivery apparatus for implanting a prosthetic valve.

Dilator 88 can be used to partially expand valve 12 as the balloon 28 and the dilator 88 are moved in the proximal direction relative to the valve so that it is easier to position balloon 28 within valve 12 when preparing the valve to be expanded by balloon 28. FIGS. 21A-21C show more details of dilator 88. The cone shape of the dilator 88 permits valve 12 to expand smoothly as the dilator is moved proximally through the valve so that the balloon can slide into the valve more easily. Dilator 88 or stopper 90 can further include a marker, such as a radiopaque marker, to provide a reference point for a surgeon during the implantation procedure.

It should be understood that in the embodiments disclosed here, balloon 28 can be either pushed (or pulled) within valve 12 or valve 12 can be pushed (or pulled) onto balloon 28. For example, in the above embodiment, it may be desirable to push valve 12 over dilator 88 and onto balloon 28. The distal end of guide catheter 14 abuts the wire frame of valve 12 and by pushing or moving guide catheter 14 distally (relative to the balloon catheter 16), valve 12 can be moved into position for deployment on top of balloon 18.

Referring to FIG. 21A, dilator 88 has an opening 92 through which nose catheter 18 can pass. In addition, as shown in FIG. 21B, dilator 88 can have two slotted sections 94. Slotted sections 94 extend longitudinally along the length of dilator 88. Slotted section 94 permit fluids to flow between the front and back areas of dilator 88.

Figure 23A:
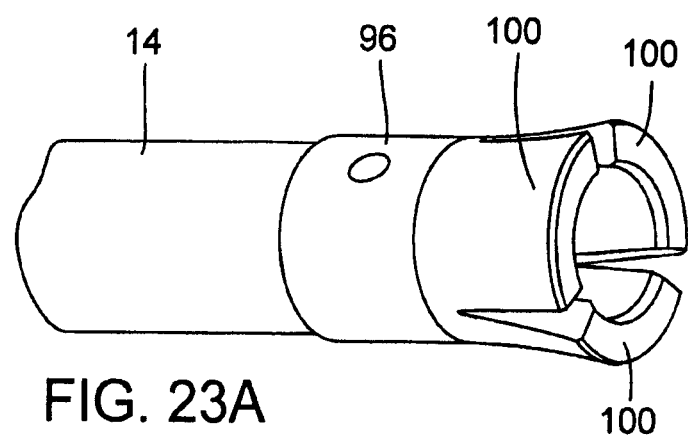
FIG. 23A is a perspective view of a flex tip attached to a distal end of a catheter for use with an endovascular delivery apparatus for implanting a prosthetic valve.
Figure 23B:
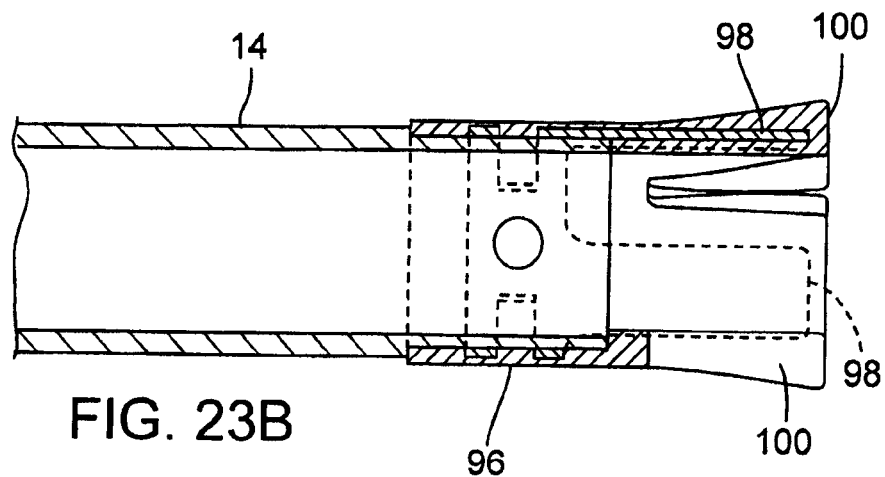
FIG. 23B is a cross section view of a flex tip attached to a distal end of a catheter for use with an endovascular delivery apparatus for implanting a prosthetic valve.

FIGS. 22A-22D show a flex adapter 96 and FIGS. 23A and 23B show a flex adapter 96 positioned on a distal end of a guide catheter 14. Flex adapter 96 has a plurality of spaced-apart fingers 98 (three in the illustrated embodiment). Flex adapter 96 can be positioned on the distal end of guide catheter 14 and an end member 100 can be overmolded and/or laser welded to the distal end of guide catheter 14. End member 100 can be overmolded onto the three spaced-apart fingers 98 so that it has three sections corresponding to the three spaced-apart fingers 98.

Flex adapter 96 can be formed of a resilient material, such as Nitinol, that naturally pushes the three sections of the end member 100 outward, but at the same time permits the three sections to be forced inward under pressure to form a lower profile. Thus, the three sections of end member 100 can be compressed to a smaller profile when inserted into an introducer sheath. Accordingly, the distal end of the guide catheter 14 can fit into the introducer sheath when subjected to the inwardly directed radial pressures of the introducer sheath. Upon exiting the introducer sheath, however, the three sections 100 of guide catheter expand again to the profile shown in FIG. 23A. The radially outward expansion of the three sections 100 causes the distal edge of guide catheter 14 to butt up against the frame of the crimped valve 12, which helps maintain the position of the valve 12 relative to the guide catheter 14 during maneuvering of the delivery apparatus.

Also, the expansion of the three sections 100 (shown in FIG. 23A) can make it easier for a balloon member to be pulled or pushed underneath a crimped valve in the manners discussed above. In addition, the sectioned flex adapter 96 and the sectioned distal end of the guide catheter 14 permit expansion of the distal end of the guide catheter 14 so that a balloon can be expanded while the balloon is at least partially contained by the distal end of the guide catheter 14.

Figure 24:
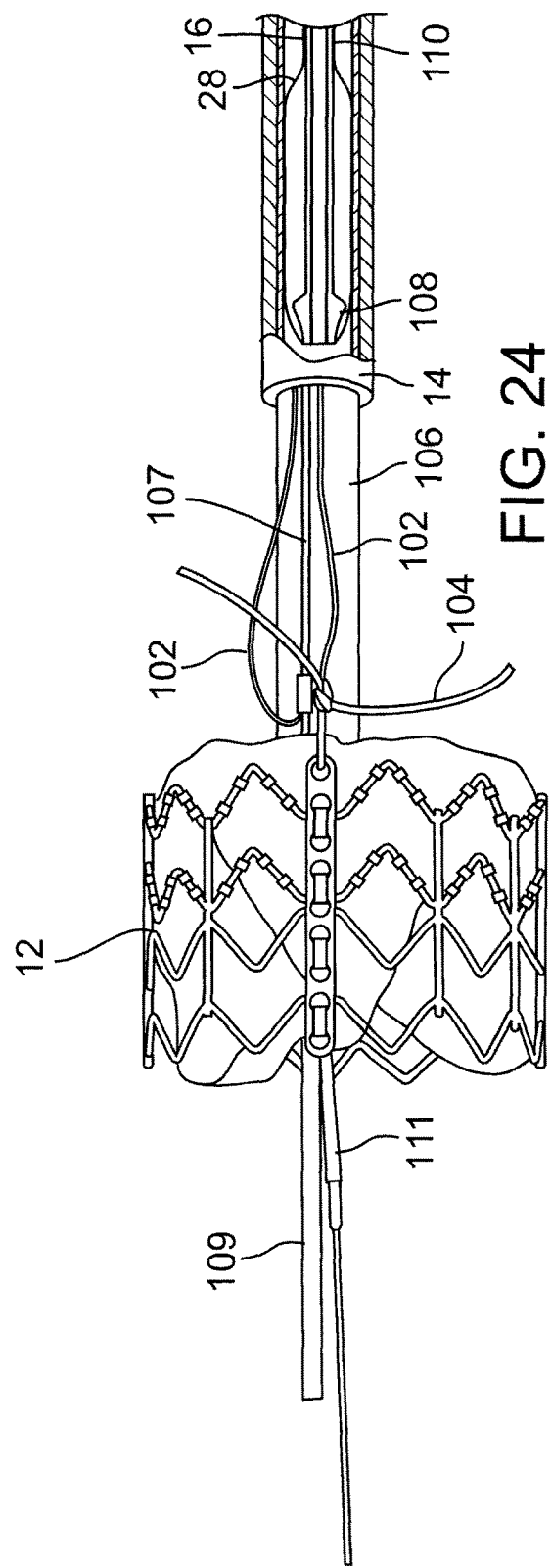
FIG. 24 is a side view of an endovascular delivery apparatus for implanting a prosthetic valve, shown partially in section.

FIG. 24 shows another embodiment of a delivery apparatus wherein a valve 12 can be located and crimped distal to a balloon 28 on an inner sleeve 106. A distal end of a guide wire 109 extends beyond the distal end of valve 12. A hypotube 111 can extend at least partially into the valve to facilitate the transfer of valve 12 to the delivery apparatus.

The inner sleeve 106 is desirably formed of one or more of the materials discussed above, including Nitinol, stainless steel, or polymers such as nylon, PET, PEEK, PE, Pebax, Urethane, and PVC. Valve 12 can be temporarily secured to a wire loop 102 and a distal end of a separate wire member 107. Valve 12 is desirably tied to wire member 107 and wire loop 102 using a suture 104 or other type of temporary tying connection. Desirably, valve 12 is tied to wire loop 102 and wire member 107 in such a manner that the suture 104 connection can be released by pulling on a proximal end of wire member 107, which can extend the entire length of the guide catheter 14. In operation, by pulling or moving wire member 107 in the proximal direction, valve 12 is released and suture 104 remains secured to wire loop 102. Wire loop 102 can extend the length of the guide catheter 14 and can be removed from guide catheter 14 by pulling wire loop 102 through the shaft of the guide catheter 14.

By tying valve 12 so that its movement is restricted in the distal direction relative to the distal end of guide catheter 14, balloon 28 can be more easily pushed under valve 12. The tying of valve 12 to the distal end of the guide catheter 14, as discussed above, can be combined with each of the embodiments herein to further secure the valve 12 relative to the guide catheter.

Certain embodiments above discuss using second balloon elements to partially expand valve 12 to make it easier to move the main balloon 28 into position beneath valve 12. FIG. 24 illustrates another example of the use of a second balloon 108 to facilitate positioning of main balloon 28. Second balloon 108 can be positioned inside of balloon 28 at the distal end of balloon 28. The distal end of balloon catheter 16 can be moved partially under a crimped valve 12. Second balloon 108 can then be inflated via a second balloon inflation lumen 110 so that the portion of second balloon 108 that is within crimped valve 12 partially expands valve 12. If desired, second balloon 108 can then be deflated and moved distally so that second balloon 108 is disposed further within valve 12. Second balloon 108 can then be inflated again so that the area of valve 12 that is now on top of second balloon 108 can be expanded. By deflating second balloon 108 and moving it distally further within valve 12 until the entire valve 12 is expanded (or until valve 12 is expanded sufficiently to receive balloon 28 within it), valve 12 can be uniformly, partially expanded so that balloon 28 can be easily positioned within valve 12 for deployment of the valve. That is, if desired, second balloon 108 can be inflated, deflated, and repositioned repeatedly so that valve 12 is sufficiently expanded to permit the larger main balloon 28 to be maneuvered beneath valve 12.

When crimping the valve proximal to the balloon in the embodiments discussed above, the valve is desirably crimped so that the leaflets fold outward, toward the outflow end of the valve and in the proximal direction of the delivery apparatus. In this manner, when pulling the balloon back (proximally) through the valve so that the balloon is positioned beneath the valve, the balloon is pulled back in the direction of the folded leaflets. Thus, the movement of the balloon into position beneath the valve is more efficient and the likelihood that the leaflets will interfere with the movement of the balloon is minimized. Damage to the leaflets from the movement of the balloon is also less likely to occur because the movement of the balloon is in the same direction as the leaflets of the valve.

Figure 25:
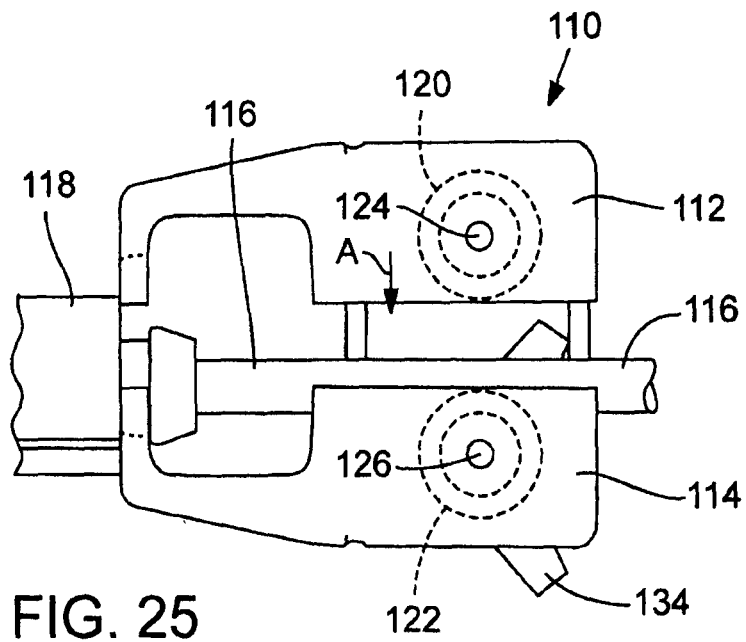
FIG. 25 is a side view of an embodiment of a catheter advancement device, shown in a partially open position.
Figure 26:
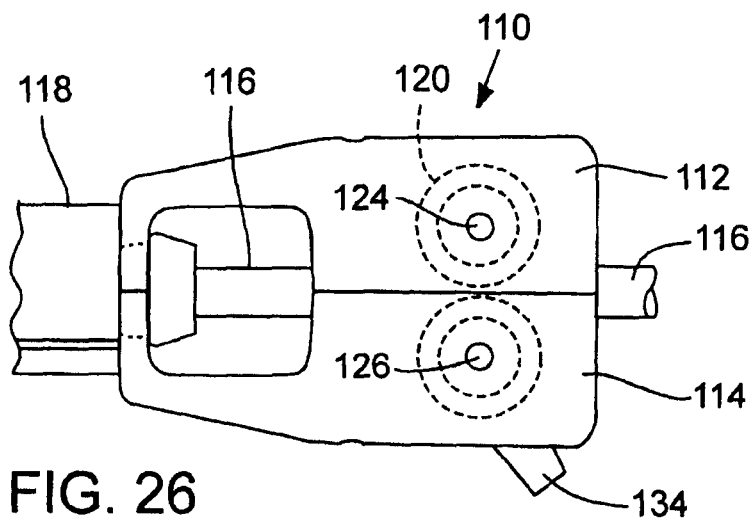
FIG. 26 is a side view of the catheter advancement device of FIG. 25.
Figure 27:
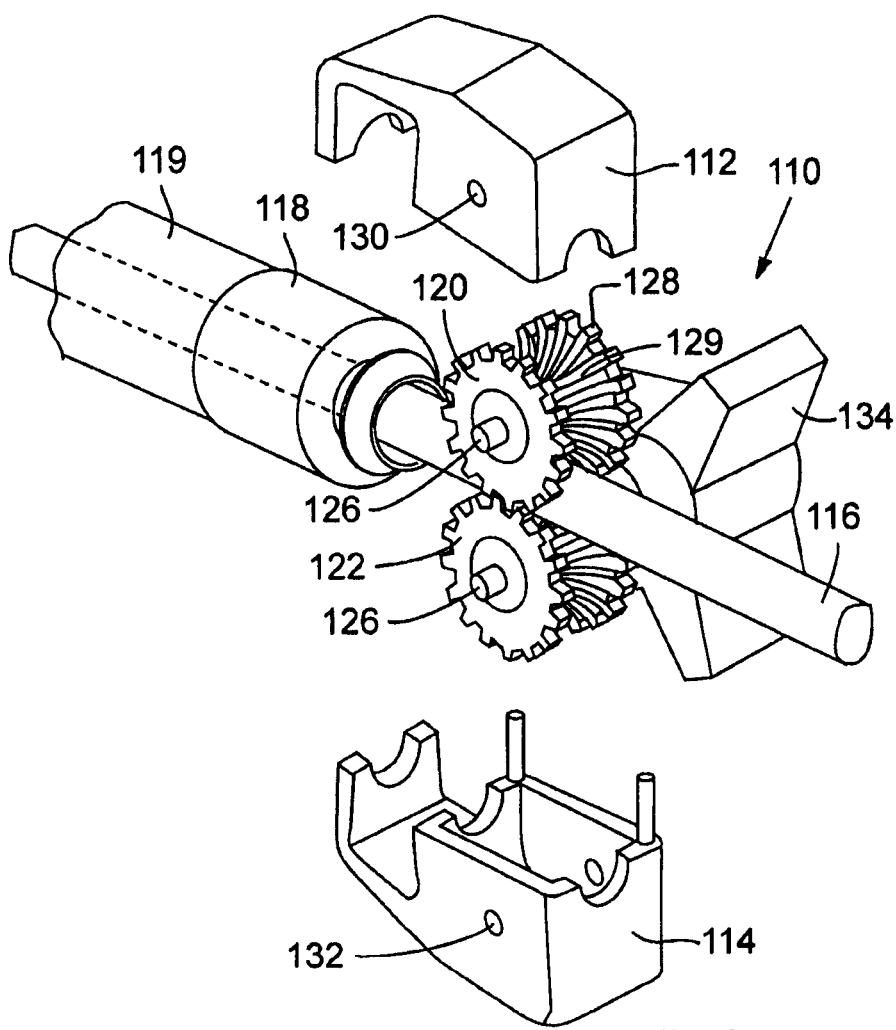
FIG. 27 is an exploded perspective view of the catheter advancement device of FIG. 25.

FIGS. 25-27 show an embodiment of an apparatus for mechanically maneuvering a catheter or other tube through the vasculature of a patient. In the below embodiment, a method and apparatus is disclosed in which an advancement apparatus is clamped over a guide catheter as it is being inserted through a femoral access introducer sheath and seal housing. The apparatus facilitates the advancement of the guide catheter through the introducer sheath by reducing the amount of force a surgeon must apply to pass the guide catheter through the introducer sheath, while at the same time providing the surgeon with sufficient control of the advancement of the guide catheter. Although the apparatus is discussed below in the context of advancing a catheter for deployment of a prosthetic valve, the apparatus can be utilized in other operations or procedures where a mechanical assist is necessary or useful to push or pull one tube or catheter axially relative to another catheter or platform.

Advancement apparatus 110 includes a top member 112 and a bottom member 114. FIG. 25 depicts the top member 112 and bottom member 114 separate from one another, while FIG. 26 shows the top member 112 and bottom member 114 in closed position and locked onto an introducer sheath 119 (shown in FIG. 27) and a guide catheter 116. The top and bottom members 112, 114 are closed onto and over guide catheter 116 in the direction of arrow A shown in FIG. 25. In addition, top and bottom members 112, 114 close onto and over a proximal end of a locking member 118, which prevents introducer sheath 119 from moving relative to apparatus 110.

Introducer sheath locking member 118 (or retaining member) locks onto the proximal end of an introducer sheath 119. The mechanism for locking onto the sheath housing can be any mechanical locking mechanism, including, for example a snap-fit or press-fit connection that firmly holds the sheath housing to the sheath locking member 118. Alternative or additional mechanical means may be useful to ensure that the locking member 118 does not move relative to the sheath housing.

The guide catheter 116 is disposed between a top gear member 120 and a bottom gear member 122. Top and bottom gear members 120, 122 have a top and bottom axle member 124, 126 (respectively). Top and bottom axle members 124, 126 fit into openings 130, 132 (respectively) in the top and bottom members 112, 114. The top and bottom gear members 120, 122 can have teeth 128, which frictionally engage the outer surface of guide catheter 116. The advancement apparatus includes a drive member 134, which in FIG. 27 is a rotating knob. Drive member 134 drives the bottom gear member 122, the teeth of which engage the teeth of the top gear member 120. By rotating the drive member 134, the teeth on the bottom gear member 122 drive guide catheter 116 in the direction of the rotating force. In addition, since the teeth on the bottom gear member 122 also drive the teeth on the top gear member 120, the top gear member 120 also drives guide catheter 116 in the direction of the rotating force.

Because locking member 118 of advancement apparatus 110 locks onto the sheath housing, the resultant forces are canceled out and the advancement of the guide catheter through the introducer sheath can be more easily controlled. In addition, because the net force is zero, it is less likely that the introducer sheath will be inadvertently pulled out of the patient's body during advancement of the guide catheter by a surgeon.

Teeth 128 include spanning grip members 129, which span between opposing teeth 128 that are on opposite sides of a gear member. Spanning grip members 129 form a concave arc between opposing teeth 128, with the arc tracking the general shape of the shaft of guide catheter 116. Grip members 129 desirably comprise an elastomeric material that is selected to provide sufficient gripping force for gripping the guide catheter. The friction caused by pressing spanning grip members 129 against guide catheter 116 causes spanning grip members 129 to grip the shaft of the guide catheter 116 to ensure that a steady application of force to the drive member 134 results in a steady movement of the guide catheter 116.

The gear members can be provided with one-way bearings so that the drive member 134 can be used as a ratchet handle. That is, drive member 134 can be configured such that it can be advanced only in one direction. When the drive member 134 is formed with a one-way ratcheting mechanism, the knob (or other manual adjustment member) can be released during operation without the guide catheter from being forced backwards by forces within the introducer sheath that are resisting the advancement of the guide catheter. This also reduces the risk that the guide catheter 116 will be pulled backwards by the surgeon while it is in the introducer sheath, which could damage the valve or cause it to be dislodged from its crimped location relative on the delivery apparatus. When the valve has cleared the distal end of the introducer sheath, the advancement apparatus 110 can be removed from the guide catheter to allow tracking and deployment to continue without the advancement apparatus 110.

FIG. 27 shows the advancement apparatus with two gears that have teeth on both the drive wheel (bottom gear member 122) and the idler wheel (top gear member 120). In this manner, guide catheter 116 is driven by both wheels at the same time. However, the driving mechanism can vary and the guide catheter 116 can be driven by one gear or more than two gear members. In addition, the gearing or gear ratio of the driving mechanism can vary. The gear members can also vary in size and holding power (break torque), and can be configured to provide an override at a certain torque. In addition, various handle options can be attached to advancement apparatus 110.

Friction between the gear members and the guide catheter is very important to provide for a controlled delivery of guide catheter 116 by advancement apparatus 110. Accordingly, the size, shape, rigidity, and surface of gear members can vary to provide an appropriate amount of friction (or grip) necessary to drive the guide catheter.

Figure 28:
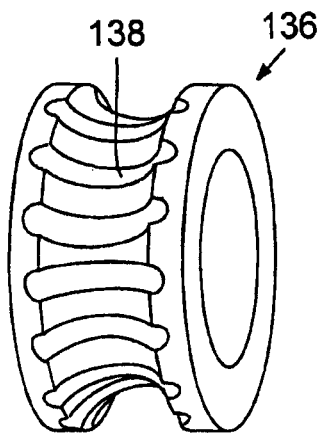
FIG. 28 is a perspective view of a gear member for use with a catheter advancement device.
Figure 29:
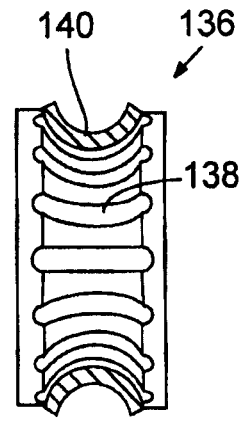
FIG. 29 is an end view of another gear member for use with a catheter advancement device.
Figure 30:
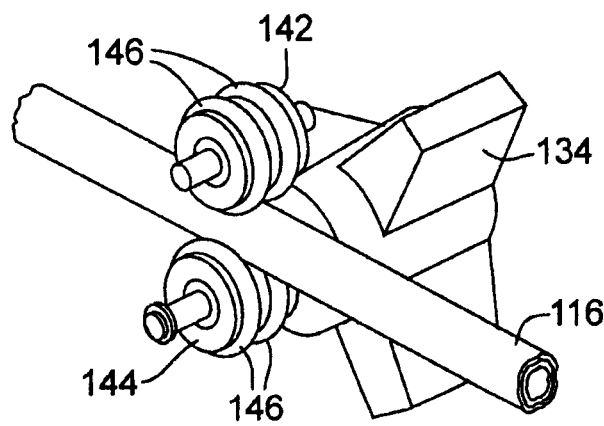
FIG. 30 is a partial perspective view of an embodiment of an advancement device, with certain elements removed for clarity.

FIGS. 28-30 show alternative gear members that can be used to drive guide catheter 116 in connection with the advancement apparatus 110. FIG. 28 shows a gear member 136 with a central concave shape with recesses 138 for gripping a guide catheter. The number and depth of the recesses can vary depending on the amount of friction or grip needed for the application. Gear member 136 can be a single driving gear member without gear teeth to connect it to a second gear member. Alternatively, gear member 136 can have gear teeth on it so that two gear members can drive a guide catheter.

FIG. 29 shows gear member 136 with an additional gripping material 140 disposed in at least some of recesses 138. Gripping material 140 can be attached to recesses 138 in any convention manner, and can be attached to some or all of the recesses 138. Gripping material 140 provides an increased frictional contact between gear member 136 and guide catheter 116. Gripping material 140 can be an elastomeric material, such as silicone, rubber, or other elastic polymers. These materials are capable of increasing the friction between gear member 136 and guide catheter 116, but have a contact surface that will not cause damage to the surface of guide catheter 136 during advancement.

FIG. 30 shows another embodiment of an advancement apparatus that has a top gear member 142 and a bottom gear member 144. Each of the top and bottom gear members 142, 144 comprise two o-ring members 146. Two o-ring members 146 on each gear member engage and drive guide catheter 116 when drive member 134 is rotated. Although FIG. 30 shows the bottom gear member 144 as the only driving member, the advancement apparatus of FIG. 30 could be modified with appropriate gearing so that both the top and bottom gear members drive the guide catheter 116. The o-rings can be formed of a variety of materials, including the materials discussed above with regard to the gripping material. The material of the o-rings is desirably selected so that the o-rings will not cause damage to the surface of the guide catheter when frictionally engaged with the guide catheter during advancement of the guide catheter through the introducer sheath.

In another embodiment, a flex indicating device can be used in connection with a guide catheter that is capable of flexing at its distal end. Catheters, such as guide catheters, can be provided with a flexing ability so that the catheter can be steered through a patient's vasculature. However, when steering a catheter through a patient's vasculature it can be difficult to determine how much the catheter has been flexed at any given moment.

Figure 31:
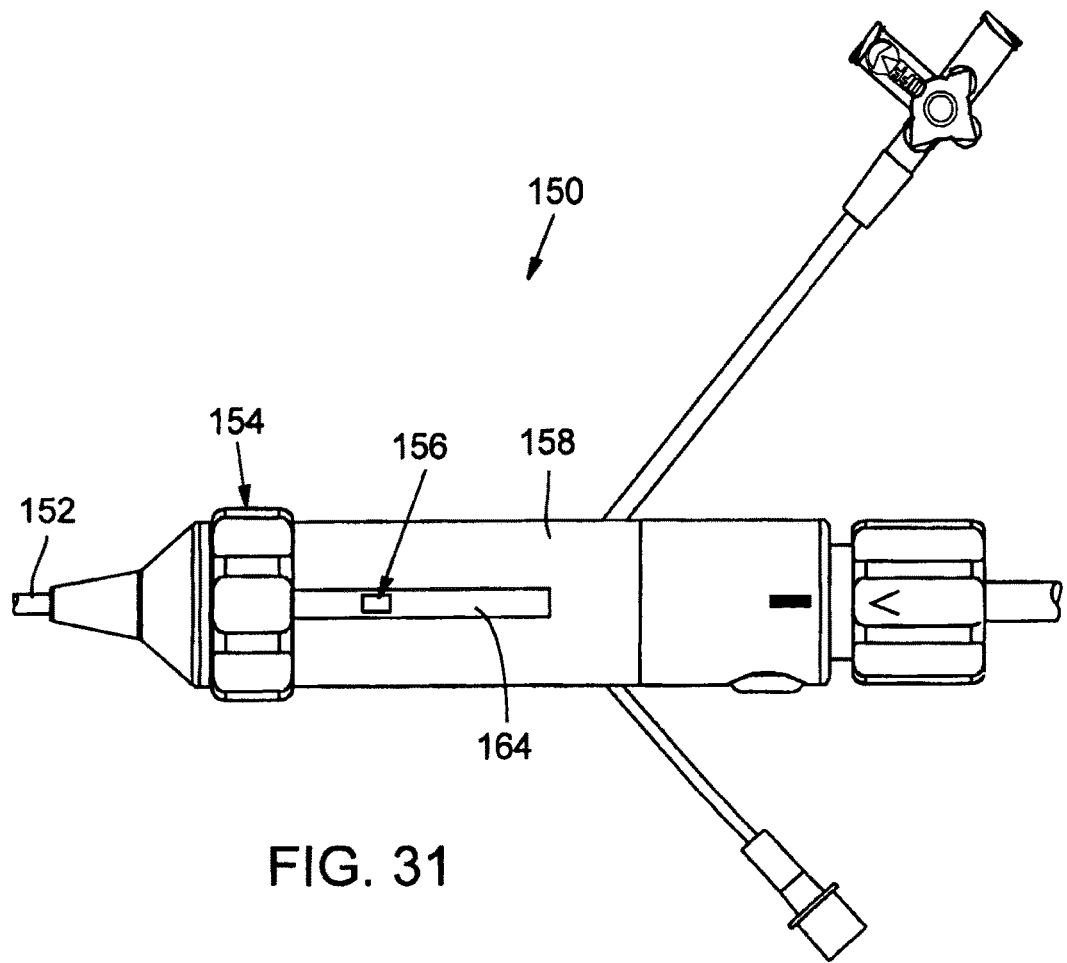
FIG. 31 is a side view of an embodiment of a flex indicating device for use in deploying a catheter into a patient's vasculature.
Figure 33:
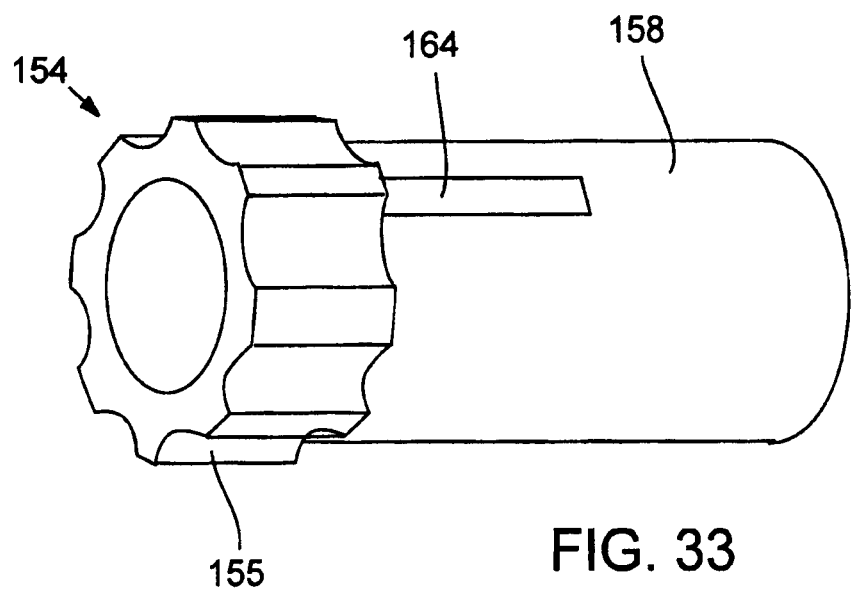
FIG. 33 is a partial perspective view of the flex indicating device shown in FIG. 31.
Figure 34:
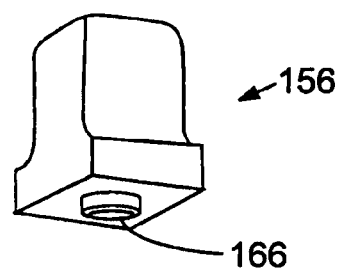
FIG. 34 is a perspective view of an indicator pin for use with the flex indicating device shown in FIG. 31.

Referring to FIG. 31, flex indicating device 150 provides a surgeon with a device for measuring the relative amount of flex of the distal end of a catheter. In addition, the indicator provides a visual and tactile response at a proximal handle end of the device, which provides a surgeon with an immediate and direct way to determine the amount of flex of the distal end of the catheter.

Flex indicating device 150 comprises a flex activating member 154, an indicator pin 156, and a handle portion 158. Flex indicating device is configured to flex a distal end of an elongated shaft 152 of a catheter (e.g., a guide catheter) by pulling on a wire (not shown) that is attached to the distal tip of the shaft 152 and which extends the length of the shaft. The pulling of the wire is achieved by rotating flex activating member 154 (e.g., a knob) that has female threads running down its length.

Figure 32:
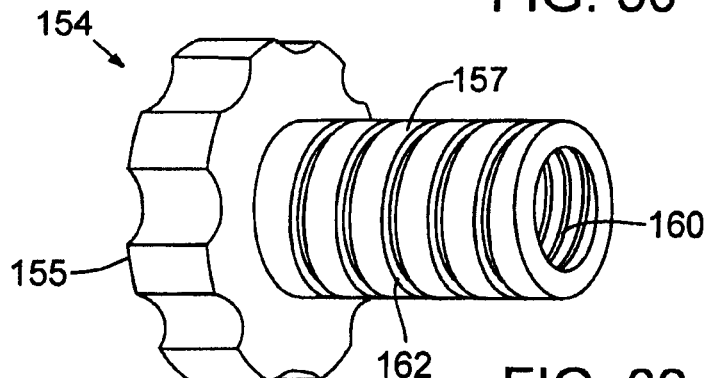
FIG. 32 is a perspective view of a flex activating member for use with the flex indicating device shown in FIG. 31.

Referring to FIG. 32, flex activating member 154 comprises an adjustment knob 155 and a shaft 157 extending from the knob. The shaft 157 has an internally threaded surface portion 160 that mates with a slide nut that has male threads. The proximal end of the wire is attached to the slide nut via a crimp pin and a counter bored hole or slot. As the flex activating member 154 is rotated, the slide nut translates along the internally threaded surface portion 160 towards the proximal end of the flex indicating device 150, thereby causing the distal end of the catheter 152 to flex. As the amount of the rotation of the flex activating member 154 increases, the slide nut moves further toward the proximal end of the flex indicating device 150 and the amount of flex of the distal end of catheter 152 increases.

The shaft 157 also includes an externally threaded surface portion 162. As shown in FIG. 37, an extending portion 166 of indicator pin 156 mates with the externally threaded surface portion 162 of flex activating member 154. The shaft 157 extends into the handle portion 158 and the indicator pin 156 is trapped between the externally threaded surface portion 162 and the handle portion 158, with a portion of the indicator pin 156 extending upward into a longitudinal slot 164 of the handle. As the knob 155 rotated to increase the flex of the distal end of the shaft of catheter 152, indicator pin 156 tracks the external threaded portion 162 of the flex activating member and moves in the proximal direction inside of slot 164. The greater the amount of rotation of the flex activating member 154, the further indicator pin 156 moves towards the proximal end of handle 158. Conversely, rotating the knob 155 in the opposite direction decreases the flex of the distal end of the shaft of the catheter and causes corresponding movement of the indicator pin 156 toward the distal end of the handle.

Figure 35A:
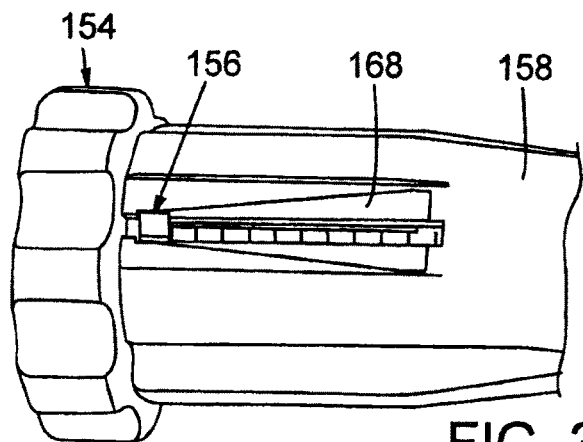
FIG. 35A is a partial perspective view of a flex indicating device.
Figure 35B:
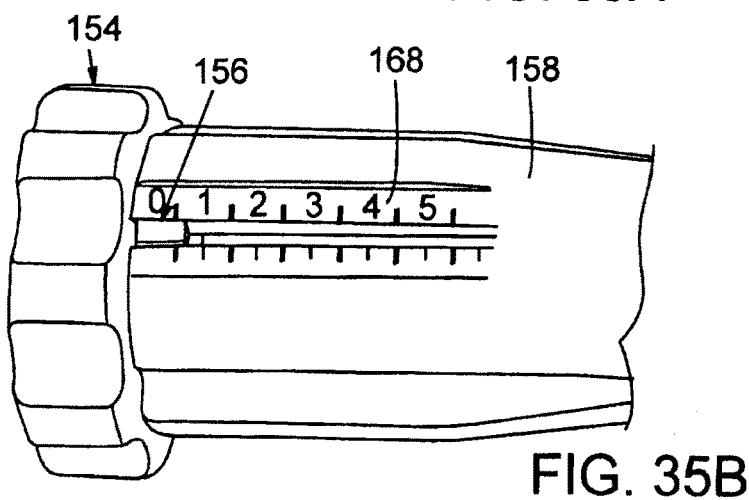
FIG. 35B is a partial perspective view of a flex indicating device.

Referring to FIGS. 35A and 35B, the flex indicating device 150 desirably includes indicia 168 that indicate the amount of flex of the distal end of catheter 152. Indicia 168 can identify the amount of flex in any of a variety of manners. For example, FIG. 35 shows indicia 168 depicting the amount of flex using a triangular marking system while FIG. 36 shows indicia 168 depicting the amount of flex using numbers.

Figure 36:
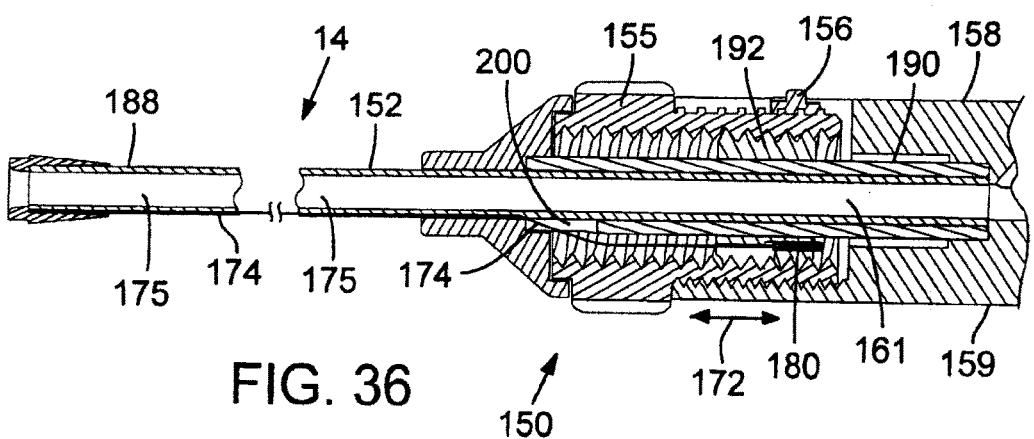
FIG. 36 is a partial cross section view of a handle portion of a flex indicating device with an elongated shaft that has a steerable section at a distal end.

The handle portion 158 is shown in greater detail in FIG. 36. As discussed above, the flex indicating device 150 (e.g., a guide catheter) includes a handle portion 158 and an elongated guide tube, or shaft, 152 extending distally therefrom. The guide tube 152 defines a lumen 175 sized to receive the shaft of the balloon catheter and allow the balloon catheter to slide longitudinally relative to the guide catheter. The distal end portion of the guide tube 152 comprises a steerable section 188, the curvature of which can be adjusted by the operator to assist in guiding the apparatus through the patient's vasculature, and in particular, the aortic arch.

The handle portion 158 includes a main body, or housing, 159 formed with a central lumen 161 that receives the proximal end portion of the guide tube 152. The handle portion 158 can include a side arm 62 (as shown in FIG. 1) defining an internal passage which fluidly communicates with the lumen 161. A stopcock can be mounted on the upper end of side arm 62.

The handle portion 158 can be operatively connected to the steerable section and functions as an adjustment to permit operator adjustment of the curvature of the steerable section via manual adjustment of the handle portion. In the illustrated embodiment, for example, the handle portion 158 includes an inner sleeve 190 that surrounds a portion of the guide tube 152 inside the handle body 159. A threaded slide nut 192 is disposed on and slidable relative to the sleeve 190. The slide nut 192 is formed with external threads that mate with internal threads of an adjustment knob 155. Sleeve 190 also has an external threaded portion that mates with an extension member of a flex indicating member 156. Flex indicating member 156 is shown in more detail in FIG. 37.

Slide nut 192 can be formed with two slots formed on the inner surface of the nut and extending the length thereof.

Sleeve 190 can be formed with longitudinally extending slots that are aligned with the slots of the slide nut 192 when the slide nut is placed on the sleeve. Disposed in each slot is a respective elongated nut guide, which can be in the form of an elongated rod or pin. The nut guides extend radially into respective slots in the slide nut 192 to prevent rotation of the slide nut 192 relative to the sleeve 190. By virtue of this arrangement, rotation of the adjustment knob 155 (either clockwise or counterclockwise) causes the slide nut 192 to move longitudinally relative to the sleeve 190 in the directions indicated by double-headed arrow 172.

One or more pull wires 174 connect the adjustment knob 155 to the steerable section 188 to produce movement of the steerable section upon rotation of the adjustment knob. In certain embodiments, the proximal end portion of the pull wire 174 can extend into and can be secured to a retaining pin 180, such as by crimping the pin 180 to the pull wire. The pin 180 is disposed in a slot in the slide nut 192. The pull wire 174 extends from pin 180, through a slot in the slide nut, a slot 200 in the sleeve 190, and into and through a pull wire lumen in the shaft 152. The distal end portion of the pull wire 174 is secured to the distal end portion of the steerable section 188.

The pin 180, which retains the proximal end of the pull wire 174, is captured in the slot in the slide nut 192. Hence, when the adjustment knob 155 is rotated to move the slide nut 192 in the proximal direction, the pull wire 174 also is moved in the proximal direction. The pull wire pulls the distal end of the steerable section 188 back toward the handle portion, thereby bending the steerable section and reducing its radius of curvature. The friction between the adjustment knob 155 and the slide nut 192 is sufficient to hold the pull wire taut, thus preserving the shape of the bend in the steerable section if the operator releases the adjustment knob 155. When the adjustment knob 155 is rotated in the opposite direction to move the slide nut 192 in the distal direction, tension in the pull wire is released. The resiliency of the steerable section 188 causes the steerable to return its normal, non deflected shape as tension on the pull wire is decreased. Because the pull wire 174 is not fixed to the slide nut 192, movement of the slide nut in the distal direction does not push on the end of the pull wire, causing it to buckle. Instead, the pin 180 is allowed to float within the slot of the slide nut 192 when the knob 155 is adjusted to reduce tension in the pull wire, preventing buckling of the pull wire.

In particular embodiments, the steerable section 188 in its non-deflected shape is slightly curved and in its fully curved position, the steerable section generally conforms to the shape of the aortic arch. In other embodiments, the steerable section can be substantially straight in its non-deflected position.

The handle portion 158 can have other configurations that are adapted to adjust the curvature of the steerable section 188. One such alternative handle configuration is shown co pending U.S. patent application Ser. No. 11/152,288 (published under Publication No. US 2007/0005131), which is incorporated herein by reference in its entirety. Additional details relating to the steerable section and handle configuration discussed above can be found in U.S. patent application Ser. No. 11/852977 (published as U.S. Publication No. US2008/0065011), which is incorporated herein by reference in its entirety.

The indicator pin can be formed in a variety of shapes. For example, as shown in FIGS. 38A and 38B, the indicator pin can have one or more extending portions 166. Additional extending portions may be useful to stabilize the indicator pin in the slot, as well as to provide a more accurate reading or measurement of flex.

FIGS. 39A-39C show an alternative embodiment of a delivery apparatus, indicated at 500. The delivery apparatus 500 allows a valve 12 to be mounted on a balloon 28 of a balloon catheter inside a body vessel. The balloon catheter can have a construction similar to the balloon catheter shown in FIGS. 2A and 2B except that in the embodiment of FIGS. 39A-39C, the balloon catheter shaft 526 has a distal end portion 504 that extends distally from the balloon 28 and an annular tapered wedge 502 is disposed on the distal end portion 504 adjacent the balloon. The tapered wedge 502 functions to expand the valve to facilitate positioning the same on the balloon inside the body, as further described below. The wedge 502 desirably is made from a low-friction material, such as nylon, to allow the valve to easily slide over the wedge and onto the balloon.

The delivery apparatus includes a nose catheter comprising a shaft 506 and a nose piece 508 connected to the distal end of the shaft 506. The nose catheter shaft 506 can have a guide wire lumen to receive a guide wire 540 so that the apparatus can be advanced over the guide wire with the guide wire passing through the lumen. The delivery apparatus 500 can further include a guide catheter comprising a guide catheter shaft 22 and an elongated cover 510 extending from the distal end of the shaft 22. The nose catheter, balloon catheter, and guide catheter are moveable longitudinally relative to each other and can have locking mechanisms at the proximal end of the apparatus for retaining the catheters at selected longitudinal positions relative to each other, as described in detail above.

As shown in FIG. 39A, the valve 12 is initially mounted in a crimped state on the nose catheter shaft 506 between the nose piece 508 and the tapered wedge 502, rather than on the balloon prior to inserting the delivery apparatus into the body. The valve is crimped onto the nose catheter shaft such that that valve can still move along the shaft when it is desired to place the valve on the balloon 28. The nose piece 508 can be formed with a stepped bore comprising a first bore portion 512 and a second, enlarged bore portion 514 at the proximal end of the nose piece. The stepped bore can be formed with an annular shoulder 516 extending between the first and second bore portions and adapted to engage the distal end of the valve 12 when the valve is inserted into the second portion 514. The nose piece 508 can have an outer surface that tapers in a direction toward the distal end of the nose piece 508 to provide atraumatic tracking through tortuous vasculature. The cover 510, which can be optional, is adapted to extend over and cover the balloon 28, the wedge 502, and at least a proximal end portion of the valve 12 when the valve is positioned on the nose catheter shaft for delivery. In the illustrated embodiment, the distal end of the cover 510 can be positioned to abut the proximal end of the nose piece 508 so as to completely enclose the valve during delivery. In alternative embodiments, the cover 510 can be shorter in length so that less of the outer surface of the valve or the balloon is covered during delivery.

The nose piece 508, when moved proximally relative to the balloon catheter (in the direction indicated by arrow 518), pushes the valve 12 over the wedge 502 and onto the balloon 28. As the valve passes over the wedge, the valve expands slightly to facilitate positioning the same on the balloon. The balloon catheter shaft 26 can have radiopaque markers 520 (FIG. 39A) to assist the operator in aligning the valve at the proper location on the balloon. The nose piece can have an outer layer 522 formed from a relatively soft and flexible material and an inner layer 524 formed from a relatively harder material. The inner layer 524 in the illustrated embodiment forms the shoulder 516 and the inner surface of the first bore portion 512. In this manner, the nose piece exhibits sufficient rigidity to push the valve 12 over the wedge and onto the balloon and provides a soft outer surface to minimize trauma to the body vessels. For example, the outer layer 522 can be made of 55D Pebax® and the inner layer can be made of 72D Pebax®, which is stiffer than 55D Pebax®.

The section of the delivery apparatus mounting the valve typically defines the maximum outer diameter of the apparatus inserted into the body. By mounting the valve 12 on the nose catheter shaft rather than on the balloon prior to insertion into the body, the valve 12 can be crimped to a smaller diameter than if the valve is mounted on the balloon. Accordingly, the maximum outer diameter of the delivery apparatus can be reduced for insertion into and through the vasculature. As noted above, by reducing the maximum diameter of the delivery apparatus, it is less occlusive to the femoral artery and therefore the patient's leg can remain well perfused during the procedure. In certain embodiments, the maximum outer diameter of the cover 510 and the nose piece 508 (at its proximal end) is about 0.223 inch, which is the maximum diameter of the portion of the delivery apparatus that is inserted into the body. The wedge 502 can have a diameter at its proximal end of about 0.120 inch and the guide catheter shaft 22 can have an outer diameter of about 0.184 inch.

Explaining now the operation of the delivery apparatus 500, according to one embodiment, the valve 12 is initially mounted on the nose catheter shaft and inserted into the nose piece 508 and the cover 510. After a guide wire 540 is inserted into the body, the proximal end of the wire extending from the body can be inserted into the distal end of the guide wire lumen and the delivery apparatus 500 can be inserted into a body vessel (e.g., the femoral artery) and advanced through the body (as depicted in FIG. 39A). Alternatively, an introducer sheath can be inserted first into the body vessel, for example if a cover 510 is not provided to cover the valve 12. Subsequent to inserting the introducer sheath, the delivery apparatus can be inserted through the introducer sheath and into the body vessel.

When the distal end of the delivery apparatus is advanced to a location that is convenient to slide the valve 12 onto the balloon, the guide catheter is retracted proximally relative to the balloon catheter to advance the valve and the balloon from the cover 510. For example, if implanting a prosthetic valve within the native aortic valve, the valve and the balloon can be advanced into the ascending aorta or into the left ventricle where the valve can then be moved onto the balloon. In any case, as shown in FIG. 39B, the nose catheter can be retracted proximally to advance the valve over the wedge 502 and onto the balloon 28. Markers 520 (FIG. 39A) can be used to center the valve on the balloon. After mounting the valve on the balloon, the nose catheter can be advanced distally so as not to interfere with inflation of the balloon, as shown in FIG. 39C. The valve can then be positioned at the implantation site (e.g., within the native aortic valve) and deployed by inflating the balloon.

In another embodiment, an adjustment device is provided for adjusting the position of a balloon relative to a crimped valve. As described in the various embodiments above, a balloon catheter can extend coaxially with a guide (or flex) catheter, and a balloon member at the distal end of the balloon catheter can be positioned proximal or distal to a crimped valve. As described above in more detail, the balloon member and the crimped valve can enter the vasculature of a patient through an introducer sheath and, once the balloon member and the crimped valve reach a suitable location in the body, the relative position of the valve and balloon member can be adjusted so that the balloon member is positioned within the frame of the valve so that the valve can be expanded at the treatment site. The following embodiment provides an apparatus and method for adjusting to the position of the balloon member relative to the valve to achieve accurate alignment of the balloon member within the valve prior to deployment of the valve at the treatment site.

FIG. 40 shows an adjustment device 600. Adjustment device 600 can comprise a first portion (e.g., flex indicating portion 602), and a second portion (e.g., adjustment portion 604) located proximal to the first portion. The first portion can be a flex indicating device such as is shown and described with reference to FIG. 31. Alternatively, the first portion could be a structure that does not include flex indicating features.

As shown in FIG. 40, an elongated shaft 606 of a catheter (e.g., a guide or flex catheter) extends into a distal end of adjustment device 600. The elongated shaft 606 of the guide catheter has a proximal end 620 (shown in FIG. 42) that terminates within the first portion (flex indicating portion 602) of adjustment device 600. As described in detail in the various embodiments above, an elongated shaft 608 of a balloon catheter can extend coaxially through the elongated shaft 606 of the guide catheter. The balloon catheter can have a balloon member at a distal end. The balloon catheter can also have a proximal portion 612 that defines an inner lumen that is in communication with a lumen of the elongated shaft 608 of the balloon catheter and, during inflation of the balloon member, with a fluid pressurizing device (not shown). Proximal portion 612 can be located proximal to the adjustment device 600.

As described in more detail in the previous embodiments, when the delivery apparatus is introduced into the vasculature of the patient, the balloon member can be disposed either proximal or distal to a crimped valve member. For example, FIG. 16 depicts a valve 12 that is crimped on a delivery apparatus proximal to a balloon 28 of a balloon catheter 16. Prior to expansion of balloon 28 and deployment of valve 12 at the treatment site, balloon 28 is moved relative to valve 12 so that balloon 28 is properly positioned for inflation within the frame of valve 12. As discussed below, adjustment device 600 can be used to move balloon 28 proximally into position within the frame of valve 12.

As shown in FIG. 40, a securing mechanism 610 can be disposed in adjustment portion 604. Securing mechanism 610 can also include a locking button 622 that can lock securing mechanism 610 in an open position, permitting the elongated shaft 608 to move freely relative to the adjustment device 600. As discussed in more detail below, locking button 622 can be slidably coupled with securing mechanism 610 as shown in FIG. 42.

Referring to FIG. 41, securing mechanism 610 can comprise an upper portion 614, an opening 616, and a lower portion 618. As shown in FIG. 42, elongated shaft 608 passes through opening 616 of securing member 610. Securing mechanism 610 is biased downward (that is, downward with reference to FIG. 42) by spring 626. Spring 626 biases securing mechanism 610 by contacting lower portion 618 and providing a biasing force directed away from spring 626 towards securing mechanism 610. Elongated shaft 608 is formed with one or more grooved sections 624. As shown in FIG. 42, when a grooved section 624 is engaged by a portion of securing mechanism 610 that surrounds the opening 616 on the side of spring 626, the securing mechanism secures the elongated shaft 608 and restricts further movement of the elongated shaft 608 in the longitudinal direction relative to adjustment portion 604.

Figure 42:
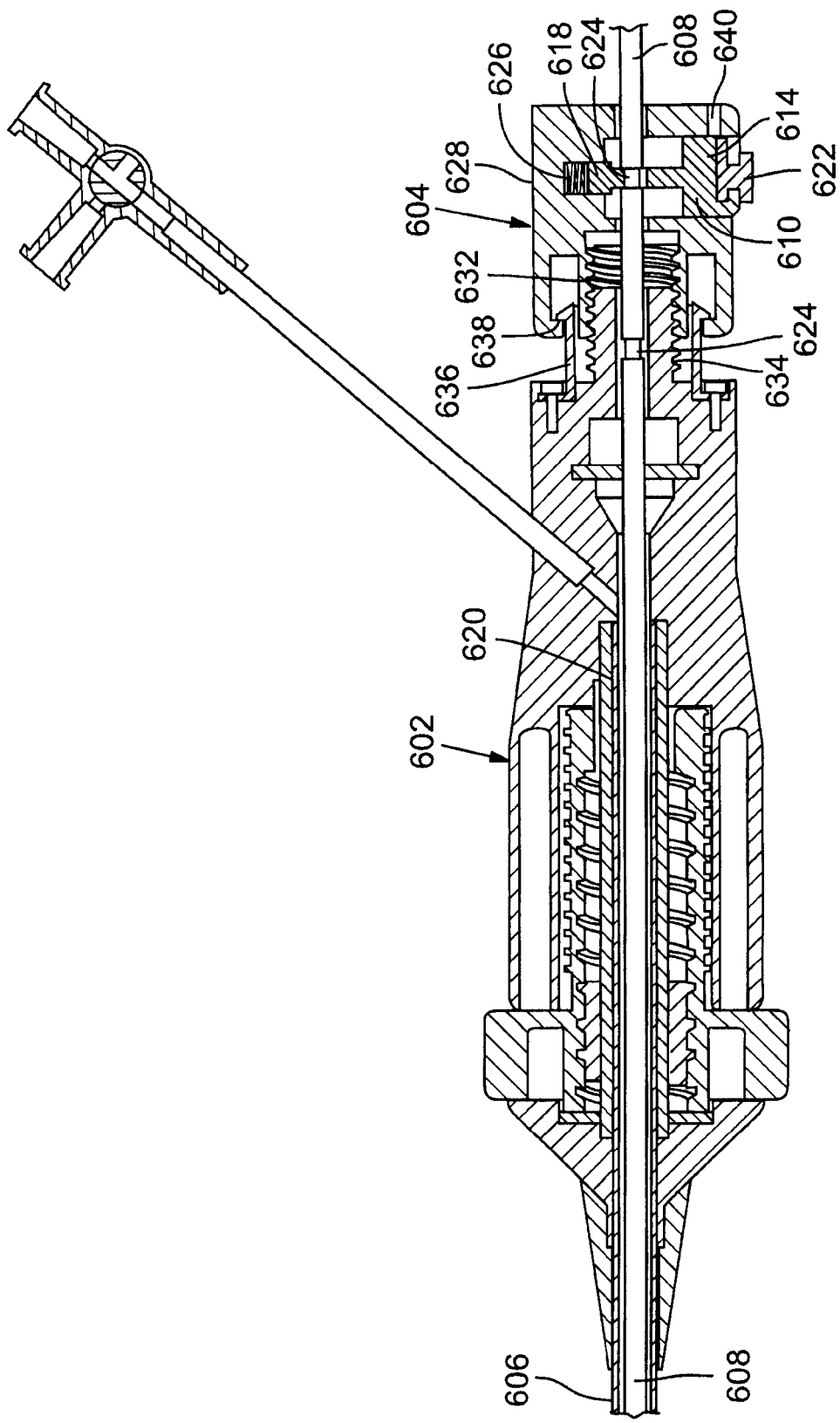
FIG. 42 is a cross section view of the adjustment device of FIG. 40.

As shown in FIG. 42, a proximal end 620 of elongated shaft 606 of the guide catheter terminates within the flex indicating portion 602 of adjustment device 600. The proximal end 620 of elongated shaft 606 of the guide catheter can be secured to flex indicating portion 602 of adjustment device 600 to prevent movement of the elongated shaft 606 relative to flex indicating portion 602. Elongated shaft 606 can be secured to flex indicating portion 602 by using, for example, an adhesive or any type of mechanical fastener. Accordingly, when securing mechanism 610 engages a grooved section 624 of elongated shaft 608, the two shafts 606, 608 are each fixed in the longitudinal direction relative to respective portions of the adjustment device 600. That is, shaft 608 is fixed relative to adjustment portion 604 (i.e., the second portion of adjustment device 600) and shaft 606 is fixed relative to flex indicating portion 602 (i.e., the first portion of adjustment device 600).

Adjustment portion 604 has an external gripping surface 628 that functions as a gripping knob or handle that can be rotated in the directions shown by arrows 630 in FIG. 40. Adjustment portion 604 can have an internally threaded portion 632 and flex indicating device portion 602 can have an externally threaded portion 634. These threaded portions can mate (or screw) together and the rotation of gripping surface 628 in a clockwise or counter-clockwise direction (as shown by arrows 630) causes adjustment portion 604 to move closer to, or further away from, flex indicating portion 602, which in turn causes shaft 608 to move axially relative to shaft 606. Accordingly, when a balloon member and a crimped valve of a delivery apparatus have been advanced to a location within the vasculature of a patient where it is desirable to mount the valve on the balloon, adjustment device 600 can be utilized to accurately change the position of the balloon member relative to the guide catheter.

Figure 43A:
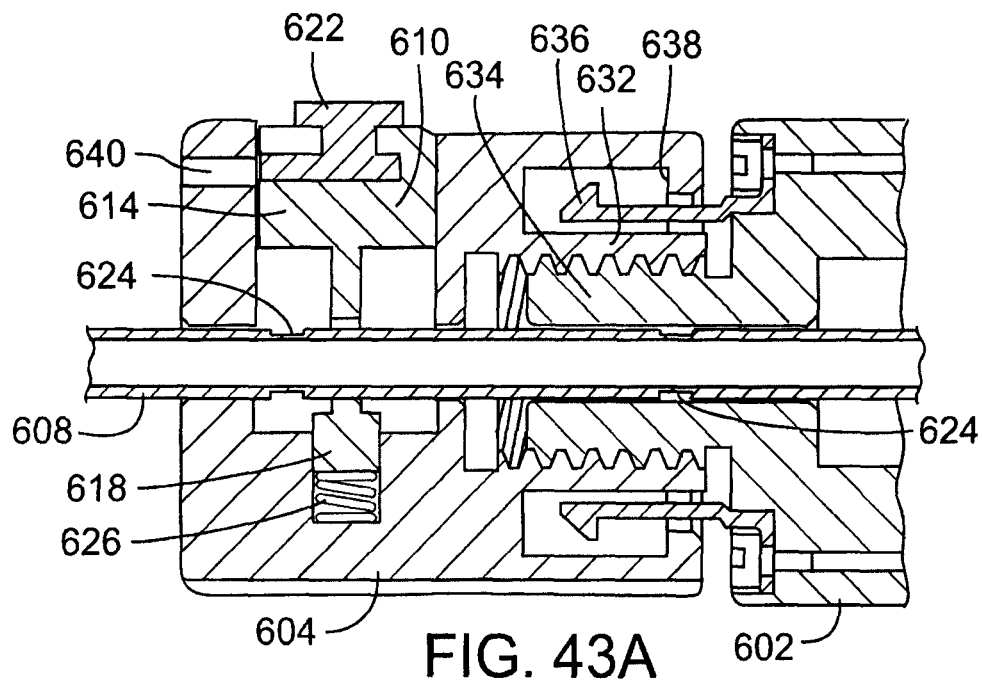
FIG. 43A is a partial cross section view of the adjustment device of FIG. 40, shown with a securing mechanism in an unsecured position.
Figure 43B:
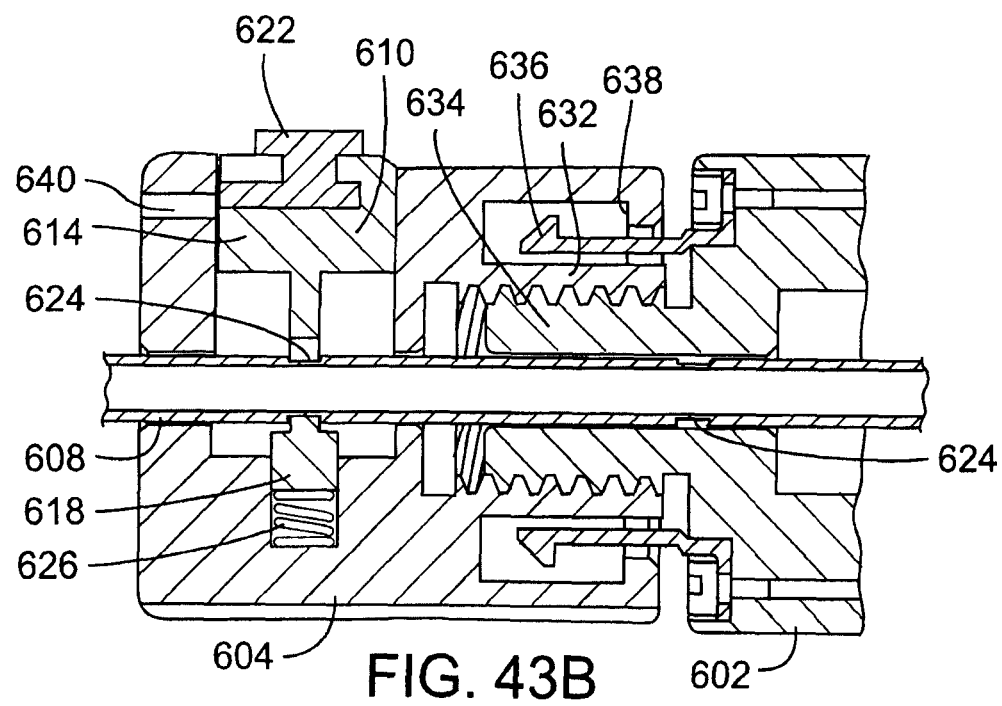
FIG. 43B is a partial cross section view of the adjustment device of FIG. 40, shown with a securing mechanism in a secured position.

Accordingly, in operation, the elongated shaft 608 of the balloon catheter can be maneuvered within the adjustment portion 604 of adjustment device 600 until a grooved section 624 of elongated shaft 608 engages securing mechanism 610. FIG. 43A shows elongated shaft 608 in a position securing mechanism 610 does not engage a grooved section, and FIG. 43B shows elongated shaft 608 in a position where a grooved section 624 is engaged by securing mechanism 610. Because securing mechanism 610 is biased toward elongated shaft 608, when a grooved section 624 passes through the opening 616 of securing mechanism 610, securing mechanism 610 automatically grips the grooved section 624, restricting longitudinal movement of elongated shaft 608 relative to adjustment portion 604. Once the securing mechanism 610 engages a grooved section 624, the longitudinal position of the balloon member can be adjusted by rotating external gripping surface 628 to move the elongated shaft 608 (and, by extension, the balloon member at the distal end of elongated shaft 608) proximal or distal towards the valve. During adjustment of the position of the balloon member relative to the valve member, an imaging technique, such as fluoroscopy, can be used to observe the relative positions of the balloon member and valve.

Figure 43C:
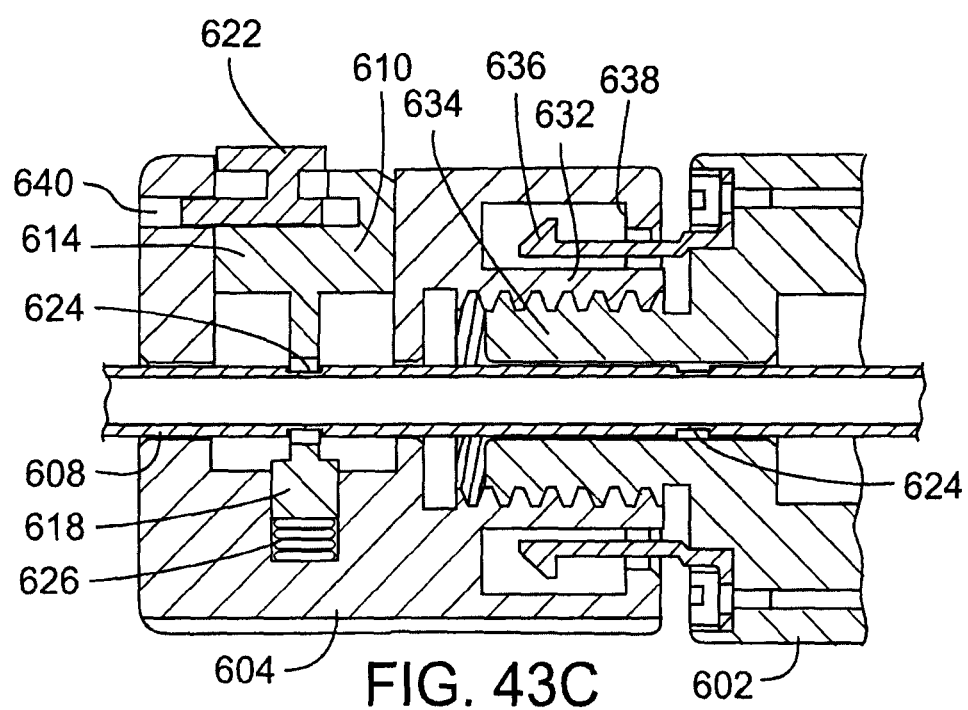
FIG. 43C is a partial cross section view of the adjustment device of FIG. 40, shown with a securing mechanism locked in an unsecured position.

As the external gripping surface 628 is rotated, adjustment portion 604 can translate proximally (or distally), pulling elongated shaft 608 and balloon member in the proximal direction (or distal direction) relative to the flex indicating portion 602. Thus, the position of elongated shaft 608 can be adjusted in a relatively slow and controlled manner. After the balloon member of the elongated shaft 608 is repositioned so that the valve is properly mounted on the balloon member, securing mechanism 610 can be released from its engagement with the grooved section by pressing securing mechanism 610 towards the spring 626 (that is, downward relative to FIGS. 43A-C).

It may be desirable at times to prevent securing mechanism 610 from locking onto the elongated shaft 608. Accordingly, locking button 622 can be configured to lock securing mechanism 610 in an "open" position against the bias of spring 626 such that the securing mechanism cannot engage one of the grooved sections 624 in the shaft 608. Locking button 622 can be coupled with securing mechanism 610. Alternatively, locking button 622 can be disposed adjacent to securing mechanism 610. An opening or slot 640 for receiving a leg portion of the locking button 622 can be provided in an adjacent wall of adjustment section 604. When securing mechanism 610 is pressed against spring 626 into an unsecured position, locking button 622 can be moved longitudinally so that the leg portion of the locking button 622 slides into opening 640. By sliding locking button 622 into opening 640, the securing mechanism 610 can be locked in an "open" position, in which elongated shaft 608 can move freely relative to adjustment portion 604. To release the locking button 622 from the "open" position, the locking button 622 can be moved back to the "unlocked" position by sliding the locking button 622 back and removing the leg portion from opening 640. This allows the securing mechanism 610 to once again engage the grooved sections 624 of the elongated shaft 608.

The amount of adjustment can vary based on the application and the length of the threads of the adjustment device 600. A desired length of available adjustment of the balloon member, for example, can be between about 2-10 mm, and more desirably between about 4-6 mm. Adjustment device 600 can be configured with threads that permit the first portion and second portion to travel to a predetermined distance from one another before the two portions separate from one another. Desirably, however, the length of travel is limited by a mechanical stop 636. Mechanical stop 636 can be formed with (or attached to) one of the first or second portions (e.g., flex indicating portion 602) and configured so that mechanical stop 636 abuts a wall portion of the opposite portion (e.g., adjustment portion 604). Mechanical stop 636 operates to prevent the first and second portions (e.g., flex indicating portion 602 and adjustment portion 604) from separating beyond a predetermined amount.

Desirably, opening 616 in securing mechanism 610 is sized and configured so that the elongated shaft 608 of the balloon catheter will not rotate along with the rotation of the adjustment portion 604. The securing mechanism and other elements of the adjustment device 600 can be formed from a variety of materials, including various plastics or metals, such as stainless steel.

There need only be one grooved section 624 that can engage with securing mechanism 610. Alternatively, the elongated shaft 608 can be formed with multiple grooved sections. The additional grooved sections can be positioned so that it is possible to adjust the relative location of the balloon member to the guide catheter at other times in the procedure, including during delivery of the valve to the treatment site or during retraction of the balloon member from the vasculature of the patient. Desirably, grooved sections 624 are positioned at locations on the elongated shaft 608 so that when the grooved section 624 engages with securing mechanism 610, the balloon member is relatively close to the desired position within the crimped valve. In this manner, the amount of distance of travel that is available between the adjustment portion 604 and the flex indicating portion 602 will be sufficient to mount the valve on the balloon member.

It should be noted that the location of the threaded portions of the adjustment device 600 can be reversed. That is, adjustment portion 604 can have an externally threaded portion and flex indicating device portion 602 can have an internally threaded portion. In addition, for embodiments where the balloon member is initially positioned proximal to the valve member, the adjustment device 600 can be configured so that the balloon member can be manipulated to move distally to be positioned within the frame of the valve member.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of delivery a prosthetic heart valve comprising:
    inserting a delivery apparatus and a prosthetic heart valve into a patient's vasculature, wherein the delivery apparatus comprises a steerable guide catheter, a balloon catheter, and a flex indicator, wherein the balloon catheter extends coaxially through the guide catheter, wherein the prosthetic heart valve is mounted on a distal end portion of the balloon catheter, and wherein the flex indicator is movably coupled to a handle of the guide catheter;
    adjusting flexion of a steerable section of the guide catheter to position the prosthetic heart valve relative to the patient's native aortic valve, wherein adjusting the flexion includes rotating a knob relative to the handle of the guide catheter, wherein the flex indicator moves longitudinally relative to the knob and relative to the handle of the guide catheter as the flexion of the steerable section is adjusted, and wherein the handle comprises one or more visual indicators adjacent the flex indicator to provide visual indication of an amount of flexion of the steerable section of the guide catheter; and
    expanding the prosthetic heart valve into contact with the patient's native aortic valve by inflating a balloon member disposed on the distal end portion of the balloon catheter.

2. The method of claim 1, wherein rotating the knob in a first direction relative to the handle of the guide catheter increases the flexion of the steerable section of the guide catheter, and wherein rotating the knob in a second direction relative to the handle of the guide catheter decreases the flexion of the steerable section of the guide catheter.

3. The method of claim 2, wherein the first direction is clockwise, and wherein the second direction is counterclockwise.

4. The method of claim 2, wherein rotating the knob in the first direction relative to the handle of the guide catheter results in the flex indicator moving toward a proximal end portion of the handle, and wherein rotating the knob in the second direction relative to the handle of the guide catheter results in the flex indicator moving toward a distal end portion of the handle.

5. The method of claim 1, wherein the handle of the guide catheter comprises an elongated slot, and wherein the flex indicator moves longitudinally in a direction parallel to a length of the slot when the flexion is adjusted.

6. The method of claim 1, wherein the one or more visual indicators include a first indicator and a second indicator, wherein the first indicator represents a non-flexed configuration of the steerable section, and wherein the second indicator represents a fully flexed configuration of the steerable section.

7. The method of claim 1, wherein adjusting the flexion includes increasing the flexion of the steerable section and decreasing the flexion of the steerable section.

8. A method of delivery a prosthetic heart valve comprising:
    inserting a delivery apparatus and a prosthetic heart valve into a patient's vasculature, wherein the delivery apparatus comprises a steerable guide catheter, a balloon catheter, and a flex indicator, wherein the balloon catheter extends coaxially through the guide catheter, wherein the prosthetic heart valve is mounted on a distal end portion of the balloon catheter, and wherein the flex indicator is movably coupled to a handle of the guide catheter;
    adjusting a curvature of a steerable section of the guide catheter as the delivery apparatus and the prosthetic heart valve are advanced through the patient's aortic arch, wherein adjusting the curvature includes rotating a knob relative to the handle of the guide catheter, wherein the flex indicator moves longitudinally relative to the knob and relative to the handle of the guide catheter as the curvature of the steerable section is adjusted, and wherein the handle comprises one or more visual indicators adjacent the flex indicator to provide visual indication of the curvature of the steerable section of the guide catheter;
    positioning the prosthetic heart valve within the patient's native aortic valve; and
    expanding the prosthetic heart valve into contact with the patient's native aortic valve by inflating a balloon member disposed on the distal end portion of the balloon catheter.

9. The method of claim 8, wherein rotating the knob in a first direction relative to the handle of the guide catheter increases the curvature of the steerable section of the guide catheter, and wherein rotating the knob in a second direction relative to the handle of the guide catheter decreases the curvature of the steerable section of the guide catheter.

10. The method of claim 9, wherein rotating the knob in the first direction relative to the handle of the guide catheter results in the flex indicator moving toward a proximal end portion of the handle, and wherein rotating the knob in the second direction relative to the handle of the guide catheter results in the flex indicator moving toward a distal end portion of the handle.

11. The method of claim 8, wherein the handle of the guide catheter comprises an elongated slot, and wherein the flex indicator moves longitudinally within the slot when the curvature is adjusted.

12. The method of claim 8, wherein the one or more visual indicators include a first indicator and a second indicator, wherein the first indicator represents a non-curved configuration of the steerable section, and wherein the second indicator represents a curved configuration of the steerable section.

13. The method of claim 8, wherein adjusting the curvature includes increasing the curvature of the steerable section and decreasing the curvature of the steerable section.

14. The method of claim 13, wherein increasing the curvature of the steerable section occurs prior to decreasing the curvature of the steerable section.

15. A method of delivery a prosthetic heart valve comprising:

inserting a delivery apparatus and a prosthetic heart valve into a patient's vasculature, wherein the delivery apparatus comprises a steerable guide catheter, a balloon catheter, an adjustment mechanism, and a flex indicator, wherein the balloon catheter extends coaxially through the guide catheter, wherein the prosthetic heart valve is mounted on a distal end portion of the balloon catheter, wherein the adjustment mechanism is movably coupled to a handle of the guide catheter, and wherein the flex indicator is movably coupled to the handle of the guide catheter;

increasing a curvature of a steerable section of the guide catheter to move the prosthetic heart valve relative to the patient's native anatomy by actuating an adjustment mechanism of the delivery apparatus, wherein actuating the adjustment mechanism includes rotating a knob of the adjustment mechanism relative to the handle of the guide catheter and relative to the flex indicator; and decreasing the curvature of a steerable section of the guide catheter to move the prosthetic heart valve relative to the patient's native anatomy by further actuating the adjustment mechanism of the delivery apparatus; and expanding the prosthetic heart valve into contact with the patient's native valve by inflating a balloon member of the balloon catheter, wherein actuating the adjustment mechanism results in the flex indicator moving longitudinally relative to the knob of the adjustment mechanism and relative to one or more visual indicators disposed on the handle adjacent the flex indicator, and wherein a position of the flex indicator relative to the one or more indicators provides a visual indication of an amount of curvature of the steerable section.

16. The method of claim 15, wherein the one or more visual indicators include a first indicator and a second indicator, wherein the first indicator represents a non-curved configuration of the steerable section, and wherein the second indicator represents a curved configuration of the steerable section.

* * * * *